(12) United States Patent
Metcalf, III et al.

(10) Patent No.: US 7,432,277 B2
(45) Date of Patent: Oct. 7, 2008

(54) PHOSPHORUS-CONTAINING MACROCYCLES

(75) Inventors: Chester A. Metcalf, III, Needham, MA (US); Leonard W. Rozamus, Bedford, MA (US); Yihan Wang, Newton, MA (US); R. Mathew Thomas, Waltham, MA (US); Dong Zou, Newton, MA (US); David L. Berstein, Waban, MA (US)

(73) Assignee: ARAID Gene Therapeutics, Inc., Cambridge, MA (US)

( * ) Notice: Subject to any disclaimer, the term of this patent is extended or adjusted under 35 U.S.C. 154(b) by 37 days.

(21) Appl. No.: 11/429,582

(22) Filed: May 5, 2006

(65) Prior Publication Data

US 2006/0264405 A1    Nov. 23, 2006

Related U.S. Application Data

(63) Continuation-in-part of application No. 10/889,163, filed on Jul. 12, 2004, now abandoned, and a continuation-in-part of application No. 10/862,149, filed on Jun. 4, 2004, now Pat. No. 7,091,213, which is a continuation-in-part of application No. 10/635,054, filed on Aug. 6, 2003, now abandoned, and a continuation-in-part of application No. 10/357,152, filed on Feb. 3, 2003, now abandoned.

(60) Provisional application No. 60/711,859, filed on Aug. 26, 2005, provisional application No. 60/486,367, filed on Jul. 11, 2003, provisional application No. 60/433,930, filed on Dec. 17, 2002, provisional application No. 60/428,383, filed on Nov. 22, 2002, provisional application No. 60/426,928, filed on Nov. 15, 2002, provisional application No. 60/353,252, filed on Feb. 1, 2002.

(51) Int. Cl.
*C07D 491/06* (2006.01)
*A61K 31/395* (2006.01)
(52) U.S. Cl. ...................... 514/291; 540/456
(58) Field of Classification Search ................ 540/456; 514/291
See application file for complete search history.

(56) References Cited

U.S. PATENT DOCUMENTS

| 5,527,907 | A | 6/1996 | Or et al. |
| 7,091,213 | B2 | 8/2006 | Metcalf et al. |
| 7,186,826 | B2 | 3/2007 | Metcalf et al. |
| 2005/0026868 | A1 | 2/2005 | Metcalf et al. |

FOREIGN PATENT DOCUMENTS

WO    WO 03/064383 A2    8/2003

OTHER PUBLICATIONS

Metcalf et al., "A novel, bone-targeted mTOR inhibitor that decreases both tumor . . . treatment of bone cancer", Abstract No. 717, AACR meeting, Apr. 5-9, 2003.
Metcalf et al., "A novel, bone-targeted mTOR inhibitor . . . treatment of bone cancer", Abstract No. 717, AACR meeting, poster presentation, Apr. 5-9, 2003.
Metcalf et al., "Bone-targeted rapamycin analogs inhibit osteolysis and tumor growth . . . bone cancer model in nude mice", Abstract No. 1116, AACR meeting, Apr. 2, 2006.
Metcalf et al., "Bone-targeted rapamycin analogs . . . bone cancer model in nude mice", Abstract No. 1116, poster presentation, AACR meeting, Apr. 2006.
Metcalf et al., "A tissue selective rapamycin analog inhibits MDA-MB-231 breast cancer . . . metastases in nude mice", Abstract No. 4857, AACR meeting, Apr. 4. 2006.
Metcalf et al., "A tissue selective rapamycin analog inhibits . . . metastases in nude mice", Abstract No. 4857, oral presentation, AACR meeting, Apr. 2006.

*Primary Examiner*—Bruck Kifle
(74) *Attorney, Agent, or Firm*—David L. Berstein; Sophie M. Binet Cross

(57) ABSTRACT

This invention concerns a new family of phosphorus-containing macrocycles containing various phosphonate- and phosphonate-containing moieties.

18 Claims, No Drawings

PHOSPHORUS-CONTAINING MACROCYCLES

This application claims priority benefit under 35 U.S.C. §119(e) to U.S. Provisional Patent Application No. 60/711,859, filed on Aug. 26, 2005 and to the following applications of which it is a continuation-in-part: U.S. patent application Ser. No. 10/889,163, filed Jul. 12th, 2004 now abandoned, which claims priority benefit under 35 U.S.C. §119(e) to U.S. Provisional Patent Application No. 60/486,367, filed on Jul. 11th 2003; and U.S. patent application Ser. No. 10/862,149, filed Jun. 4th, 2004 now U.S. Pat. No. 7,091,213,which is a continuation-in-part of U.S. patent application Ser. No. 10/635,054, filed Aug. 6, 2003 (now abandoned) and U.S. patent application Ser. No. 10/357,152, filed Feb. 3, 2003 (now abandoned). The U.S. patent application Ser. Nos. 10/635,054 and 10/357,152 claim priority under 35 U.S.C. §119(e) to U.S. Provisional Patent Application No. 60/353,252, filed Feb. 1, 2002, U.S. Provisional Patent Application No. 60/426,928, filed Nov. 15, 2002, U.S. Provisional Patent Application No. 60/428,383, filed Nov. 22, 2002 and U.S. Provisional Patent Application No. 60/433,930, filed Dec. 17, 2002. The entire contents of each of these applications are hereby incorporated by reference and the priority benefit of each application is hereby claimed.

BACKGROUND OF THE INVENTION

Cancers of the bone, both primary bone cancers and those that have metastasized to bone (bone metastases), involve complex molecular processes and have been difficult to treat. Bone metastases, a frequent consequence of common malignancies such as breast, lung and prostate cancer, are often associated with severe bone pain and pathological fractures due to increased bone fragility. Primary bone cancers (e.g., osteogenic sarcoma) present treatment challenges, and patients often require limb amputation and/or radiation therapy. In the bone microenvironment, as it is currently understood, metastasized cancer cells produce activating factors (e.g., PTHrP) that stimulate osteoclast-mediated bone resorption. Bone-derived growth factors (e.g., TGF-β and IGF1) are subsequently released, promoting cancer-cell proliferation and the amplification of a cycle that produces net osteolytic (bone destructive) consequences.

The development of new therapeutic agents for treating cancers of the bone, preferably agents that act directly and potently to inhibit bone breakdown and tumor growth would be highly desirable.

Rapamycin is a macrolide antibiotic produced by *Streptomyces hygroscopicus*. It binds to a FK506-binding protein, FKBP12, with high affinity to form a rapamycin:FKBP complex. Reported Kd values for that interaction are as low as 200 pM. The rapamycin:FKBP complex binds with high affinity to the large cellular protein, FRAP, to form a tripartite, [FKBP:rapamycin]:[FRAP], complex. In that complex rapamycin can be viewed as a dimerizer or adapter to join FKBP to FRAP. Formation of the complex is associated with rapamycin's various biological activities.

Rapamycin is a potent immunosuppressive agent and is used clinically to prevent rejection of transplanted organs. Rapamycin and/or its analogs, AP23573 (ARIAD), CCI 779 (Wyeth) and SDZ Rad ("RAD001", Novartis) are promising agents for treating certain cancers, for immune suppression and/or for helping to decrease the incidence of restenosis following interventional cardiology. Rapamycin has also been shown to have activity as an antifungal agent, in the experimental allergic encephalomyelitis model (a model for multiple sclerosis), in the adjuvant arthritis model (for rheumatoid arthritis), in inhibiting the formation of IgE-like antibodies, and for treating or preventing lupus erythematosus, pulmonary inflammation, insulin dependent diabetes mellitus, adult T-cell leukemia/lymphoma, and smooth muscle cell proliferation and intimal thickening following vascular injury. See e.g. published US Patent application 2001/0010920.

Rapamycin's potential for providing relief from such an important swath of cruel diseases has stimulated the search for rapamycin analogs with improved therapeutic index, pharmacokinetics, ease or economy of production or formulation, etc. The resulting investigation by industrial and academic researchers has led to the exploration of materials and methods for effecting chemical transformations of rapamycin, including reductions of ketones, demethylations, epimerizations, various acylations and alkylations of hydroxyls, etc.

A large number of structural variants of rapamycin have now been reported, typically arising as alternative fermentation products and/or from synthetic efforts. For example, the extensive literature on analogs, homologs, derivatives and other compounds related structurally to rapamycin ("rapalogs") include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Additional historical information is presented in the background sections of U.S. Pat. Nos. 5,525,610; 5,310,903 and 5,362,718. See also U.S. Pat. No. 5,527,907. Materials and methods have even been developed for the remarkably effective and selective epimerization of the C-28 hydroxyl group (WO 01/14387). See also U.S. Ser. No. 10/357,152 WO 03/064383 and WO 05/16252 for additional background on methods and materials for the preparation and use of rapamycin analogs containing various phosphorus-containing moieties.

New rapalogs with attractive physicochemical or functional characteristics relative to rapamycin, e.g., in therapeutic index, bioavailability, pharmacokinetics, stability, tissue distribution, etc., would also be of interest for a variety of pharmaceutical uses including among others bone cancers and other bone disorders involving bone resorption.

The three rapalogs currently in clinical development for cancer include two with conventional structural modifications, i.e., acylation or alkylation of the O at C-43 [CCI 779 and SDZ RAD, respectively; see e.g., Yu et al., Endocrine Related Cancer (2001) 8, 249-258; Geoerger et al., Cancer Res. (2001) 61 1527-1532) and Dancey, Hematol Oncol Clin N Am 16 (2002):1101-1114] and one with a rather unusual phosphine oxide substituent at that site (AP23573).

The invention described below represents a rather dramatic departure in the design of new rapalogs based on the incorporation of more elaborate phosphorus-containing moieties.

SUMMARY OF THE INVENTION

This invention provides a new family of compounds of Formula I as well as compositions and uses thereof:

Formula I

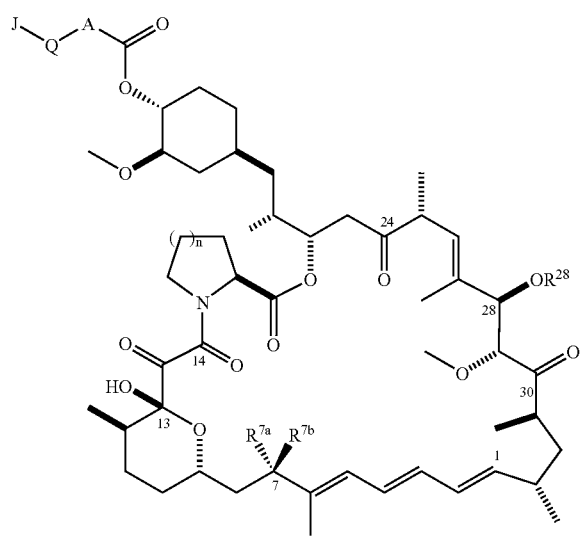

In the compounds of this invention, each occurrence of A is independently —O—, —S— or —NR²—;

Q is —V— or —VN(R)V— wherein V is independently an aliphatic, heteroaliphatic, aryl or heteroaryl moiety;

J is

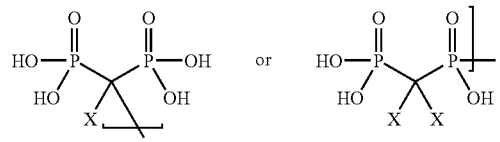

each occurrence of X is independently H, halo, —OR² or —NR²R⁵;

one of $R^{7a}$ and $R^{7b}$ is H and the other is H, halo, —OR^A, —SR^A, —OC(O)R^A, —OC(O)NR^AR^B, —NR^AR^B, —NR^BC(O)R^A, —NR^BC(O)OR^A, —NR^BSO_2R^A or —NR^BSO_2NR^AR^B; or $R^{7a}$ and $R^{7b}$, taken together, are H in the tetraene moiety:

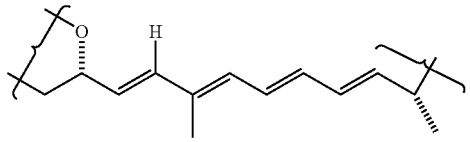

$R^A$ is $R^2$, $R^B$ is OH or $R^2$, (in some cases one or both of $R^A$ and $R^B$ is H);

R, $R^2$ and $R^5$ are independently selected from H, an aliphatic, a heteroaliphatic, an aryl and a heteroaryl moiety;

$R^{28}$ is H, —COVH or —C(O)AQJ;

and n is 1 or 2;

wherein each aliphatic moiety contains 1-8 contiguous aliphatic carbon atoms, each heteroaliphatic moiety is an aliphatic moiety which contains an O, S, N, P or Si atom in place of one or more carbon atoms; and each of the foregoing aliphatic and heteroaliphatic moieties is independently branched or unbranched, or cyclic or acyclic, and unsubstituted or substituted with one or more groups selected from halogen, —YR², —Y—C(=O)R², —NR²C(=O)R⁵, —NR²C(=O)NR⁵, —NR²C(=O)OR⁵, —NR²C(=NH)NR⁵, —Y—C(=O)OR², —Y—C(=O)NR²R⁵, —Y—C(=NR²)NR²R⁵, —COCOR², —C(=O)(CH₂)ᵣC(=O)R², J, —CN, —S(=O)R², —SO₂R², —SO₂NR²R⁵, —NO₂, —NR⁵SO₂R², —OSO₂R², —NR⁵SO₂NR²R⁵, =O, =S, =NR², =NNR²R⁵, =NNHC(O)R², =NNHCO₂R², and =NNHSO₂R², wherein Y is selected from a bond, —O—, NR⁵, and —S—, r is an integer of 1 to 4;

and each aryl or heteroaryl moiety is independently unsubstituted or substituted with one or more groups selected from halogen, —YR², —Y—C(=O)R², —NR²C(=O)R⁵, —NR²C(=O)NR⁵, —NR²C(=O)OR⁵, and —NR²C(=NR²)NR⁵, —Y—C(=O)OR², —Y—C(=O)NR²R⁵, —Y—C(=NR²)NR²R⁵, —COCOR², —C(=O)(CH₂)ᵣC(=O)R², J, —CN, —S(=O)R², —SO₂R², —SO₂NR²R⁵, —OSO₂R², —NO₂, —NR⁵SO₂R² and —NR⁵SO₂NR²R; wherein Y is selected from a bond, —O—, NR⁵, and —S—, r is an integer of 1 to 4.

This new family includes a number of classes of compounds of particular interest, including compounds of Formula II in which in which J, V, R and the other variables are as previously defined and Q is VNRV.

Formula II

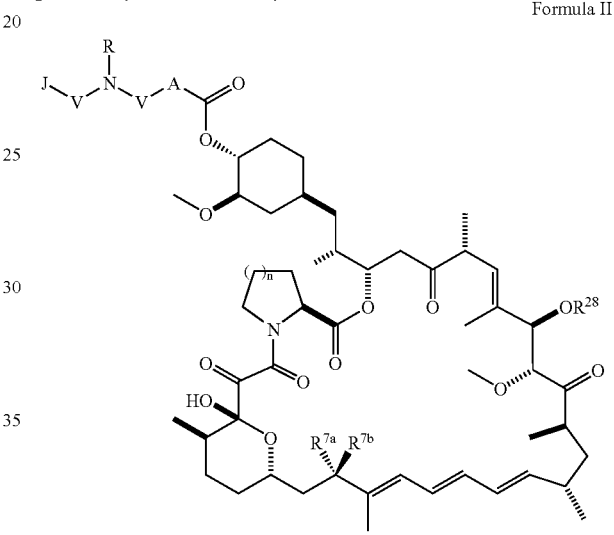

Of particular interest is an interesting subclass of compounds of Formula II in which A is $NR^2$, and the V group linking NR to $NR^2$ is $(CH_2)_m$, wherein m is an integer from 2 to 8. This subclass is represented by compounds of the Formula II(a).

Formula II(a)

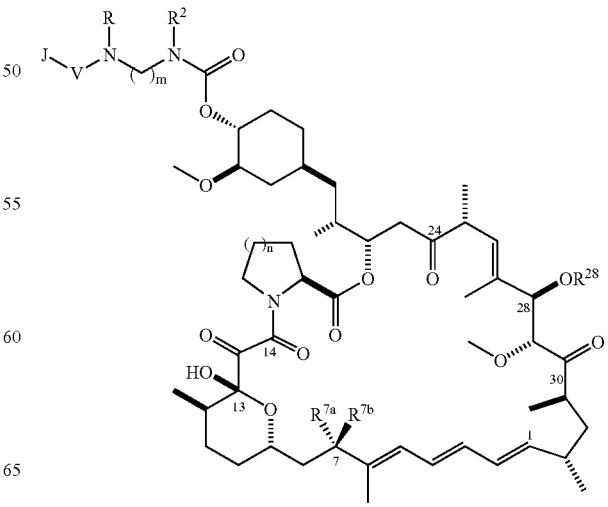

More specific compounds of Formula II(a), in which m is 2 are represented below with Formula II(b):

Examples include, among others, compounds of Formula II(d) in which the $R^2$ and R groups taken together form a 2-carbon aliphatic moiety:

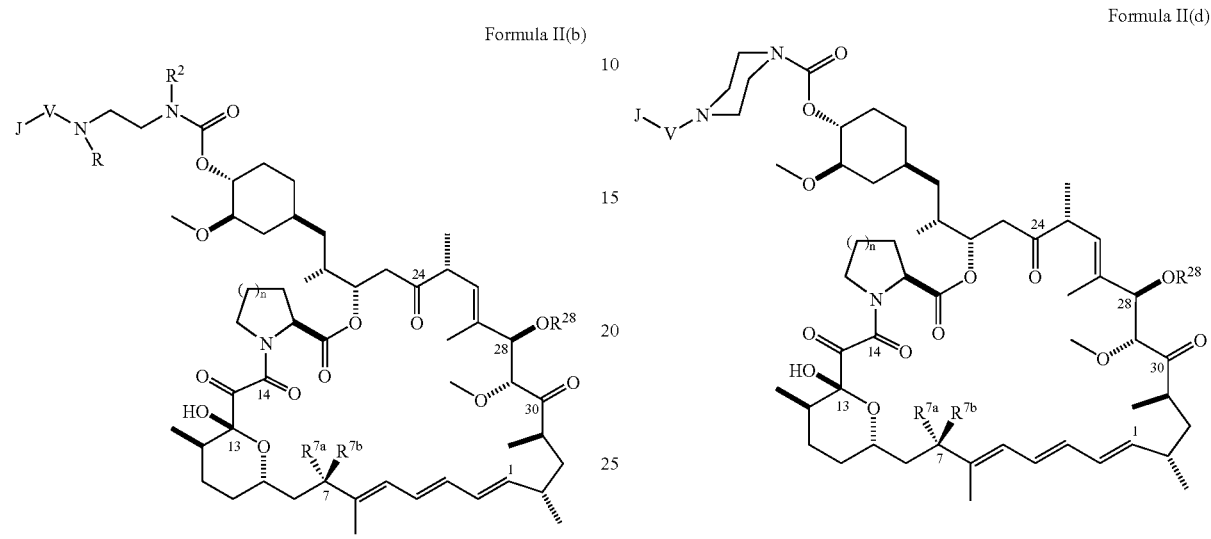

A further feature of this invention relates to compounds of Formula II(b) in which A is $NR^2$ and the groups R and $R^2$ of the moiety J-V—NR—V—$NR^2$—, are taken together to form an aliphatic or heteroaliphatic group, $V^1$, as illustrated in Formula II(c), below:

Compounds of particular current interest include those of Formulas II(a), II(b), II(c) and II(d) in which V is an aryl ring.

Other compounds of interest include those of those of Formulas II(a), II(b), II(c) and II(d) in which V is a heteroaryl ring.

Another subclass of particular interest includes compounds of Formula II in which J is a substituent of an aryl or heteroaryl moiety (V). This is illustrated by compounds of Formula II(e) in which the "distal" moiety V is a phenyl or pyridyl moiety bearing the substituent, J:

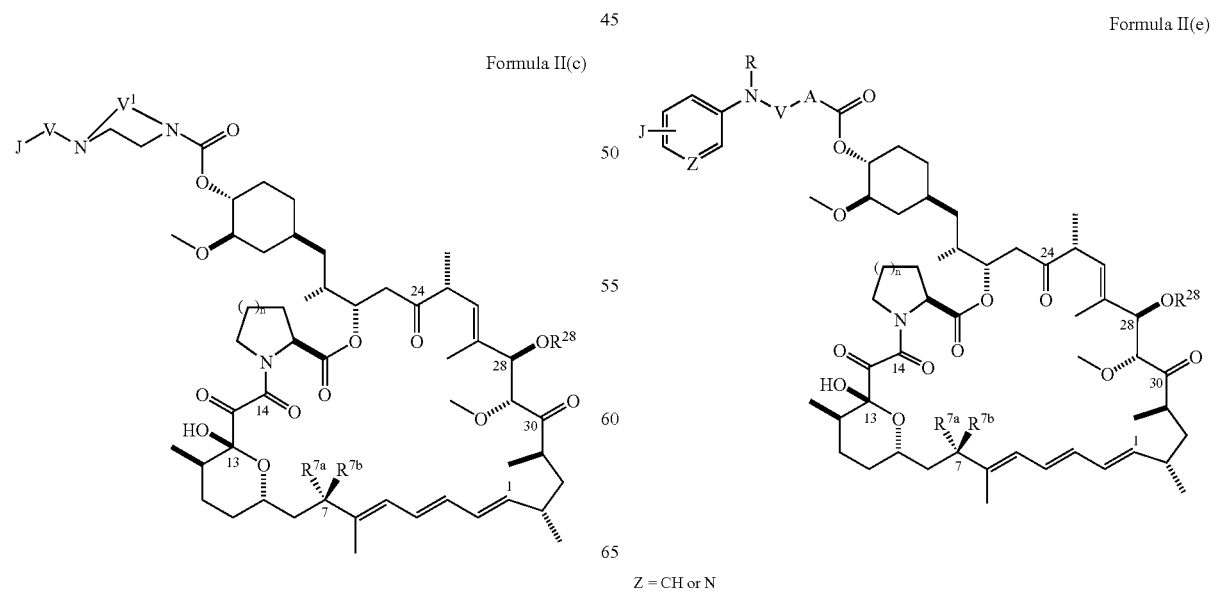

Z = CH or N

In some cases V in compounds of Formula II(e) is an aliphatic group, while in others it is an aryl or heteroaryl moiety.

Another subclass of particular interest includes compounds of Formula II in which A is —NR$^2$—, such as those of Formulas II(b) and II(c), where in the —NR—V—NR$^2$— group, the R$^2$ group is hydrogen. In some cases, the R group is also a hydrogen while in other cases, the R group is a C$_{1-8}$ alkyl group, such as methyl, ethyl, i-propyl, t-butyl, etc . . .

Another subclass of interest includes compounds of Formula II which contain an —NR—V—NR$^2$— group, as in the preceding paragraph, but in which the R$^2$ group is a C$_{1-8}$ alkyl group, such as methyl, ethyl, i-propyl, t-butyl, etc . . . ; and the R group is in some cases hydrogen, while in other cases of particular interest, the R group is also a C$_{1-8}$ alkyl group.

Compounds of particular current interest include any of the foregoing compounds with one or more of the following additional characteristics:

n is 2,

R$^{28}$ is H, and

R$^{7a}$ is OMe and R$^{7b}$ is H.

Also of particular interest are family members of Formula II in which V of the moiety —NR—V-A- is aliphatic, whether A is O, NR$^2$ or S, although carbamates and carbonates are of special interest. Such aliphatic groups preferably contain 1-8 contiguous aliphatic carbon atoms, and typically 2-8 carbon atoms. Such compounds include among others those in which V is a 2-4 carbon alkyl group.

Also of particular interest are family members of Formula II in which the moiety V in J-V—NR— is aryl or heteroaryl, whether A is O, NR$^2$ or S.

As indicated above, compounds of Formula II or of any of Formulae II(a) through II(e), as well as of any of the other subclasses, subsets or examples herein may contain a moiety J of the following structure:

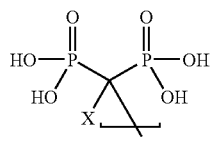

In other cases J is

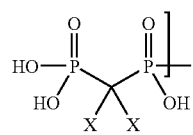

Illustrative JV— moieties include the following non-limiting examples:

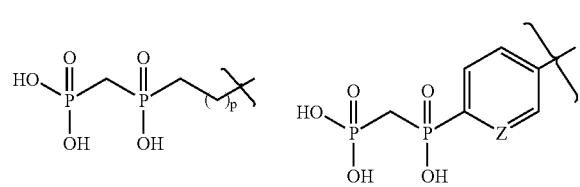

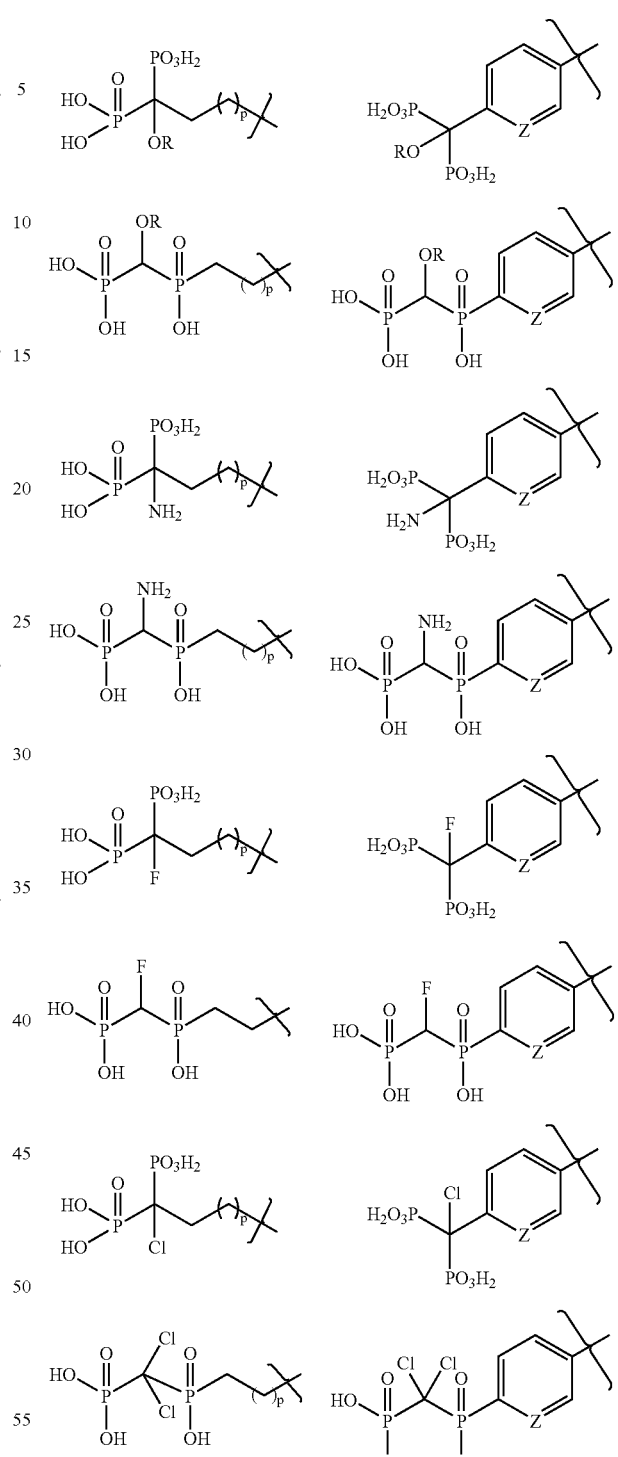

wherein p is 0, 1, 2, 3, 4 or 5 and Z is N or CH.

An Other class of compound which is of special interest for use in this invention are compounds of Formula I or formula II and Formulae II(a) through II(e), in which n is 2, R$^{28}$ is hydrogen, R$^{7a}$ is OMe and R$^{7b}$ is hydrogen.

Compounds of Formula II(b) of special interest are compounds represented below in formula II(f).

Formula II(f)

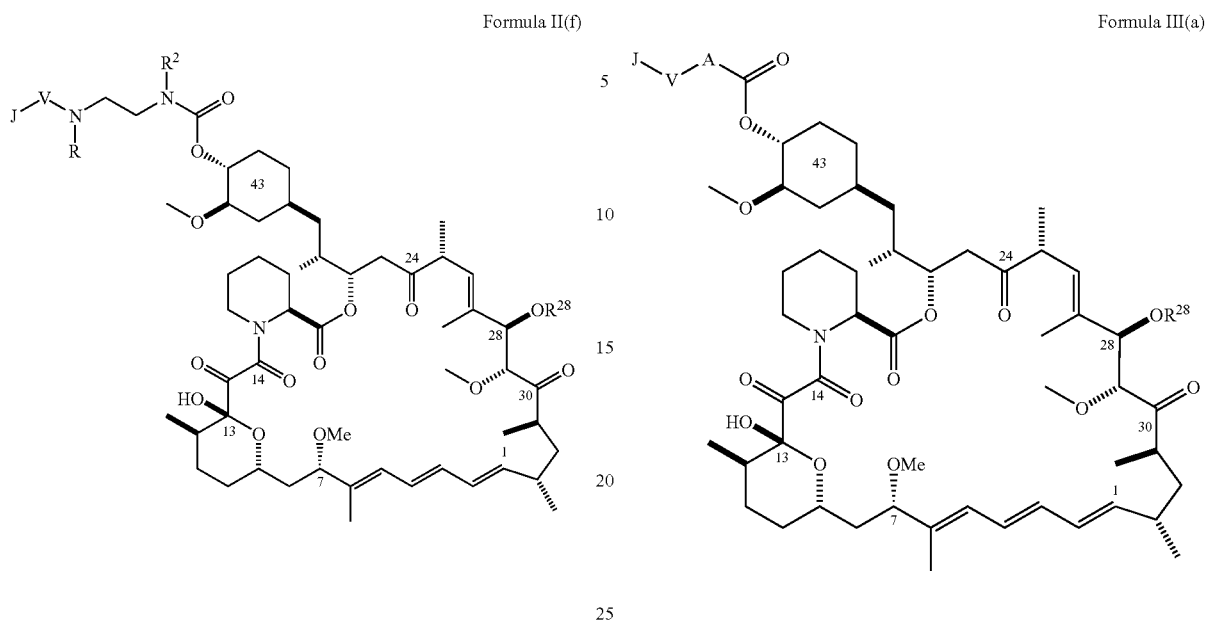

Formula III(a)

where J, V and R and $R^2$ are as defined with respect to Formula I, including without limitation all of the examples of such moieties herein, including the JV— examples noted in the preceding paragraph.

An other class of compound of interest are compounds of Formula I in which Q is V, which is represented in Formula III.

Of particular interest are family members of Formula III(a) in which A is —$NR^2$—, including the subset of such carbamates shown in Formula III(b):

Formula III

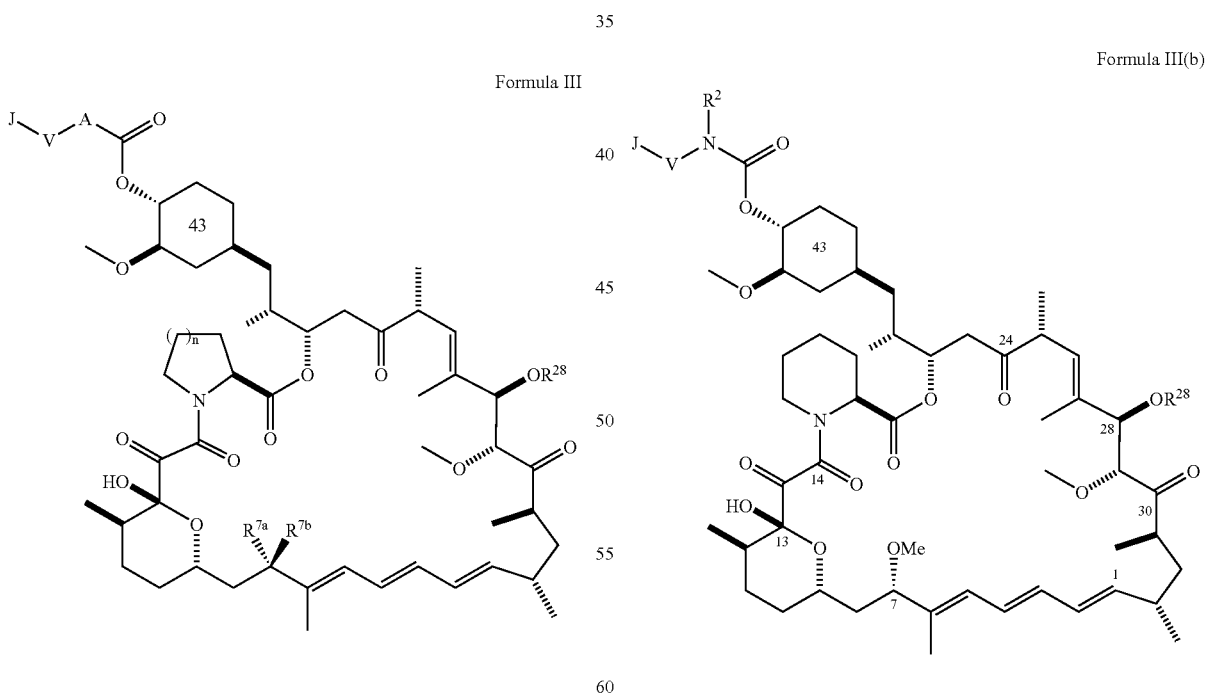

Formula III(b)

Of particular interest is a subclass of compounds of Formula III in which n is 2, $R^{28}$ is hydrogen, $R^{7a}$ is OMe and $R^{7b}$ is hydrogen. Compounds of this type are represented in Formula III(a).

Exemplary carbamates of Formula III(b) contain JVN($R^2$)CO— groups such as are illustrated in the table which follows and in the Examples further below.

Table of Illustrative Carbamates of Formula III(b)
Where JVNR²—CO— is selected from the following:
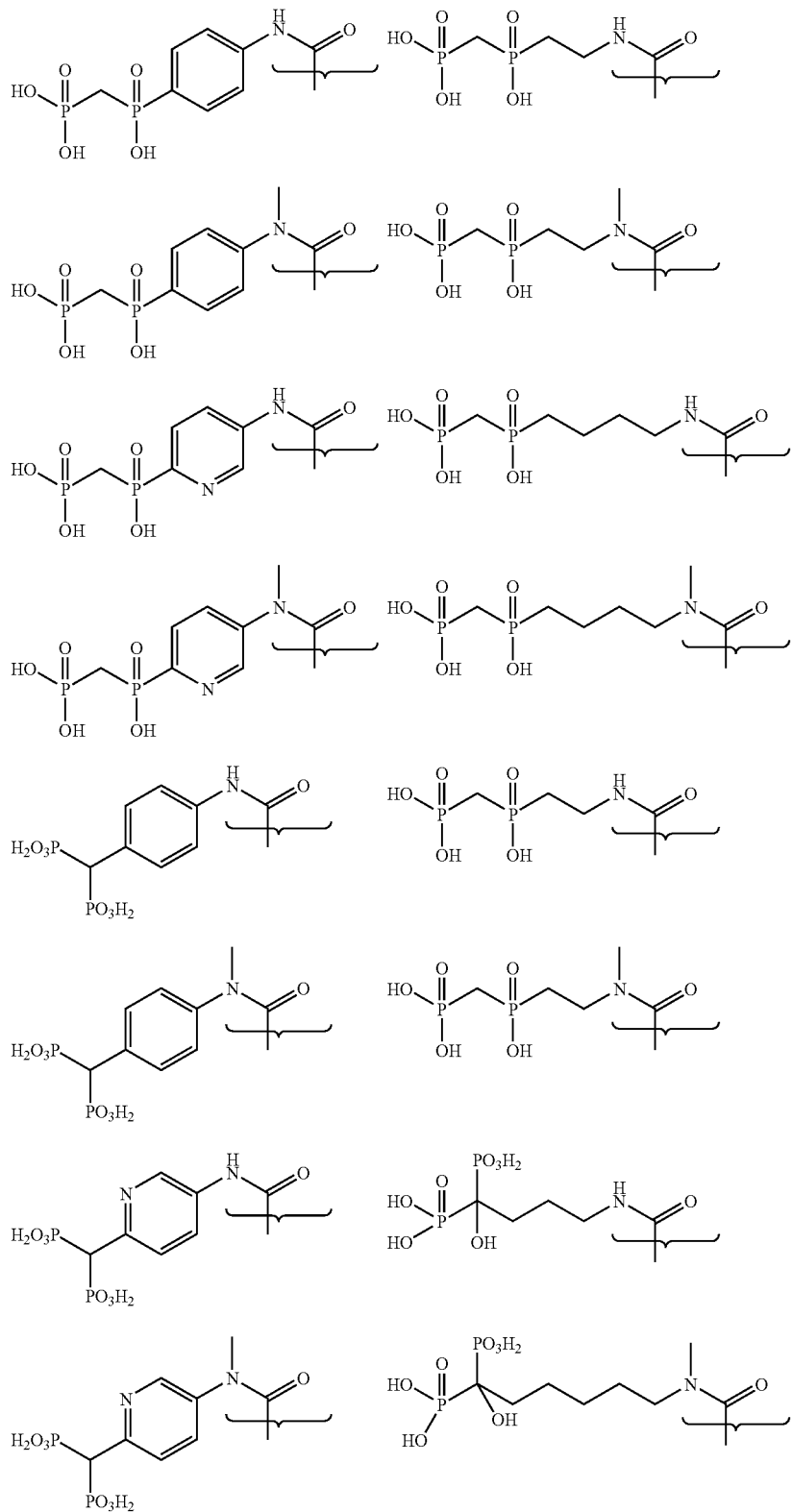

These charts are intended to be illustrative rather than comprehensive. Thus, carbamates of this invention may for example contain $R^2$ groups other than H or Me (e.g., may contain other alkyl groups, aryl groups, arylalkyl groups, etc.) and may contain aliphatic V groups of other lengths, e.g. C2 to C8, preferably C2 to C5.

Also of particular interest are family members of Formula III(a) in which A is —O—, as illustrated by compounds defined in Formula III(c):

Illustrative carbonates of Formula III(c) contain JVOCO— groups such as are illustrated in the table which follows and in the Examples further below.

Formula III(c)

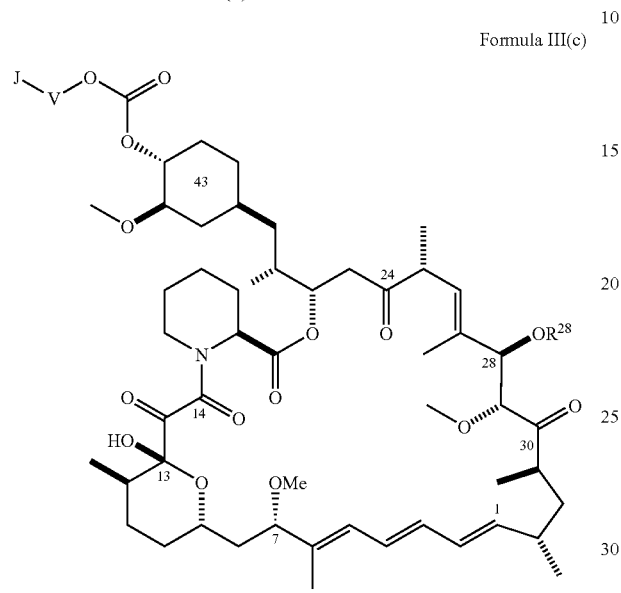

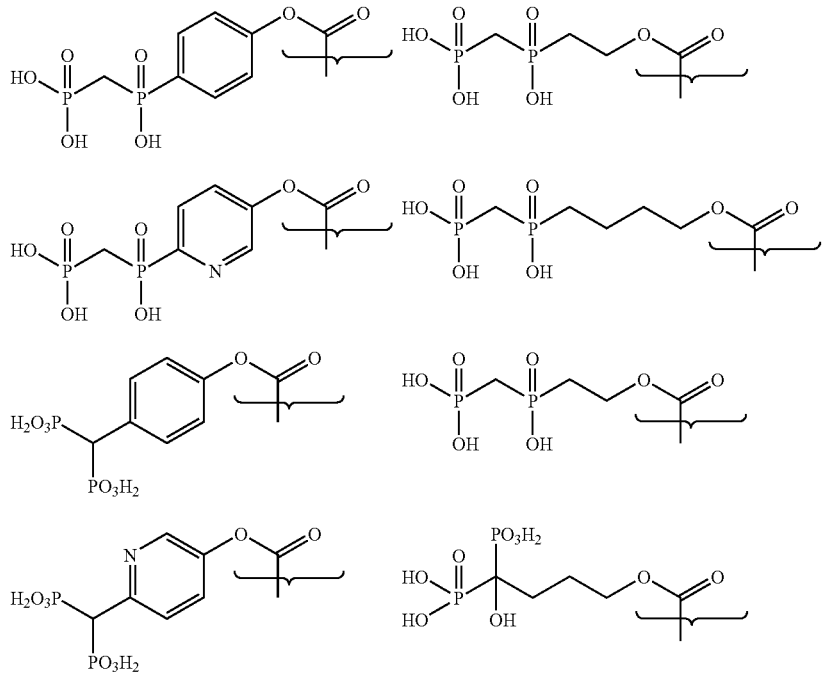

Table of Illustrative Carbonates of Formula III(c):

Where JV—O—CO— is selected from the following:

Again, such carbonates may for example contain aliphatic V groups of other lengths, e.g. C2 to C8, preferably C2 to C5.

Also encompassed by this invention are the classes, subclasses, subsets and individual compounds corresponding to those disclosed above in which A is O, rather than N.

Also of particular interest are family members of Formula III in which V is aliphatic, whether A is O, $NR^2$ or S, although carbamates and carbonates are of special interest. Such aliphatic groups preferably contain 1-8 contiguous aliphatic carbon atoms, and typically 2-8 carbon atoms. Such compounds include among others those in which V is a 2-4 carbon alkyl group. These family members include, among others, compounds of Formulas III(b) and III(c) in which V is aliphatic, preferably C1-C8 and are illustrated in the various compounds depicted above and in the Examples further below.

Also of particular interest are family members of Formula III in which V is aryl or heteroaryl, whether A is O, $NR^2$ or S. Such compounds in which V is a substituted phenyl or pyridyl group are illustrated in the Examples which follow. These family members include among others compounds of Formulas III(b) and III(c) in which V is aryl or heteroaryl. Again, carbamates and carbonates are of special interest and these family members are illustrated in the various compounds depicted above and in the Examples further below.

Additional classes of particular interest are noted below:

(a) Compounds as any of the above classes and subclasses, but with a structural modification relative to rapamycin at one or more positions additional to position 43. Numerous such modifications are known in the art and are alluded to elsewhere herein, including replacement of the —OMe substituent at C7, or alteration of its stereochemistry; epimerization at one or both of C28 and C43; reduction of one or more of the ketone functionalities e.g. at one or both of ring positions 24 and 30; desmethylation at one or more sites; reduction of one or more of the double bonds between C1 and C6; and/or use of the prolyl analog instead of the pipicolate structure of rapamycin. Compounds of this invention may be prepared by starting with the appropriate rapamycin analog in place of rapamycin itself.

(b) Compounds of the invention with a molecular below 1700, preferably below 1500, and more preferably below 1300 mass units (not counting the contribution of a counter ion in cases in which the compound is in a salt form or of a labile pro-drug moiety in the case of a pro-drug).

(c) Compounds of the invention which are chemically linked to a polyethylene glycol moiety or other solubility-enhancing group. Examples include glycinate (or other aminocarboxylate) esters or PEGylated esters (see e.g. WO 02/24706) of any free —OH moiety of a rapalog of this invention.

(d) Compounds of the invention that retain at least 0.01, preferably 0.1 and more preferably at least 0.5 times the potency of rapamycin in a T cell proliferation assay.

(e) Compounds in which one or more hydroxyl groups of one or more phosphonate and/or phosphinate groups is replaced with —$OR^2$, where each such $R^2$ group is independently chosen from methyl, ethyl, n-propyl, -propyl, n-butyl, 2-butyl, t-butyl, aryl or heteroaryl, each of which optionally bearing one or more substituents such as halo, —OH, alkoxyl-, alkoxylalkoxyl-, haloalkyl-, hydroxyalkoxyl-, acyl-, acyloxy-, heterocyclic, aryl or heteroaryl substituents.

(f) Compounds in which X is OH, or, in cases containing geminal X groups, one is OH and the other is H.

(g) Compounds in which X is $OR^2$, or, in cases containing geminal X groups, one is $OR^2$ and the other is H, where each such $R^2$ group is independently chosen from methyl, ethyl, n-propyl, -propyl, n-butyl, 2-butyl, t-butyl, phenyl, or heteroaryl, each of which optionally bearing one or more halo, —OH, alkoxyl-, alkoxylalkoxyl-, haloalkyl-, hydroxyalkoxyl-, acyl-, acyloxy-, heterocyclic, aryl or heteroaryl substituents.

Some other aspects of the invention include:

A composition comprising a compound of the invention, including any of the various types of compounds noted above, together with a pharmaceutically acceptable vehicle and optionally containing one or more pharmaceutically acceptable excipients. The composition may be one which is suitable for oral or parenteral administration to a subject, e.g. a mammalian subject, including a human patient. Compositions may be prepared using conventional materials such that they are suitable for administration by any of the routes of administration noted in this document.

The use of the compounds of this invention to prepare compositions useful for the various medical and other uses noted herein.

A method for treating osteoporosis or another bone disease involving bone resorption, graft vs. host disease, lupus, rheumatoid arthritis, diabetes mellitus, myasthenia gravis, multiple sclerosis, psoriasis, dermatitis, eczema, seborrhea, inflammatory bowel disease, pulmonary inflammation, ocular uveitis; adult T-cell leukemia/lymphoma; fungal infections; hyperproliferative restenosis; graft vascular atherosclerosis; cerebral vascular disease, coronary artery disease, cerebrovascular disease, arteriosclerosis, atherosclerosis, nonatheromatous arteriosclerosis, or vascular wall damage from cellular events leading toward immune mediated vascular damage, stroke or multiinfarct dementia in a subject in need thereof, by administering to such a subject a therapeutically effective amount of a composition containing a compound of the invention.

A method for treating cancer, especially a bone cancer, in a subject in need thereof, which comprises administering to the subject a treatment effective amount of a composition containing a compound of this invention. Various cancers which may be thus treated are noted elsewhere herein. This treatment may be provided in combination with one or more other cancer therapies, such as in combination with the administration to the subject of one or more of an anti-cancer alkylating or intercalating agent (e.g. an anthracycline such as doxorubicin, doxil, etc.); an antiestrogen; a taxane; an inhibitor of a kinase (e.g., an inhibitor of Src, BRC/Abl, kdr, aurora-2, glycogen synthase kinase 3 ("GSK-3"), cKit); an antibody to a receptor or hormone implicated in a cancer (e.g. EGFR, PDGFR, IGF-R and IL-2); or a soluble receptor or other receptor antagonist to such receptor; a proteasome inhibitor or other NF-kB inhibitor; another mTOR inhibitor [e.g., AP23573 (see e.g. WO 03/064383, esp. Example 9), rapamycin, CCI779, Everolimus, etc.]; or radiation. Examples of other therapeutic agents are noted elsewhere herein and include among others, Zyloprim, alemtuzmab, altretamine, amifostine, nastrozole, antibodies against prostate-specific membrane antigen (such as MLN-591, MLN591RL and MLN2704), arsenic trioxide, Avastin® (or other anti-VEGF antibody), bexarotene, bleomycin, busulfan, capecitabine, carboplatin, Gliadel Wafer, celecoxib, chlorambucil, cisplatin (or other platinum-based anticancer agent), cisplatin-epinephrine gel, cladribine, cytarabine liposomal, daunorubicin liposomal, daunorubicin, daunomycin, dexrazoxane, docetaxel, doxorubicin, Elliott's B Solution, epirubicin, estramustine, etoposide phosphate, etoposide, exemestane, fludarabine, 5-FU, fulvestrant, gemcitabine, gemtuzumab-ozogamicin, goserelin acetate, hydroxyurea, idarubicin, idarubicin, Idamycin, ifosfamide, imatinib mesylate, irinotecan (or other topoisomerase inhibitor, including antibodies such as MLN576 (XR11576)), letrozole, leucovorin, leucovorin levamisole, liposomal daunorubicin, melphalan, L-PAM, mesna, methotrexate, methoxsalen, mitomycin C, mitoxantrone, MLN518 or MLN608 (or other inhibitors of the flt-3 receptor tyrosine kinase, PDFG-R or c-kit), itoxantrone, paclitaxel, Pegademase, pentostatin, porfimer sodium, Rituximab (RITUXAN®), talc, tamoxifen, temozolamide, teniposide, VM-26, topotecan, toremifene, Trastuzumab (Herceptin®, or other anti-Her2 antibody), 2C4 (or other antibody which interferes with HER2-mediated signaling), tretinoin, ATRA, valrubicin, vinorelbine, or pamidronate, zoledronate or another bisphosphonate.

This invention thus provides a new family of unusual rapalogs. These compounds, rapamycin analogs modified relative to rapamycin at position 43, and optionally at C28, may also be further derivatized relative to rapamycin, e.g. at one or more of C7, C28, C13, C24 and C30 and elsewhere, by adapting chemical transformations or otherwise incorporating structural alterations such as those disclosed in U.S. Pat. No. 6,258,823, WO 96/41865, WO 98/02441, WO 99/36553 and WO 01/14387 and in the other patent documents and scientific references cited therein or within this document. Compounds of interest include among others, those which bind to human FKBP12, or inhibit its rotamase activity, within two, and more preferably within one order of magnitude of results obtained with rapamycin in any conventional FKBP binding or rotamase assay. Compounds of particular interest further include those compounds of the invention which bind to hydroxyapatite at least one, and preferably at least two orders of magnitude more strongly than does rapamycin, as determined in any scientifically valid comparative study.

Also included are salts, especially pharmaceutically acceptable salts, of the compounds of this invention. It should also be noted that the compounds of this invention may be provided in the form of a prodrug, i.e., and adduct or derivative which, upon administration to a patient, is capable of providing (directly or indirectly) a JQA-containing rapalog as described herein. A pro-drug is a derivative of a compound, usually with significantly reduced pharmacological activity, which contains an additional moiety which is susceptible to removal in vivo yielding the parent molecule as the pharmacologically active species. An example of a pro-drug is an ester or phosphonate ester which is cleaved in vivo to yield a compound of interest. Various pro-drugs of rapamycin and of other compounds, and materials and methods for derivatizing the parent compounds to create the pro-drugs, are known and may be adapted to the present invention.

Compounds of this invention may be provided in substantially pure form (relative to side products, residual reactants and other unwanted materials), e.g., at least 50% pure, suitably at least 60% pure, advantageously at least 75% pure, preferably at least 85% pure, more preferably at least 95% pure, especially at least 98% pure, all percentages being calculated on a weight/weight basis. An impure or less pure form of the compound may be useful in the preparation of a more pure form of the same compound or of a related compound (for example a corresponding derivative) suitable for pharmaceutical use.

Compounds of this invention having antifungal activity, including among others those with one or more phosphonate and/or phosphonate hydroxyl groups derivatized, and including among others those having a replacement C7 substituent in place of methoxyl, may be used as monotherapies or in combination with other antifungal agents to combat fungal infections in animals, especially mammals, including humans, in particular humans and domesticated animals (including farm animals). The compounds may be used, for example, in the treatment of topical fungal infections caused by, among other organisms, species of *Candida* (e.g. *C. albicans*), *Trichophyton* (e.g. *Trichophyton mentagrophytes*), *Microsporum* (e.g. *Microsporum gypseum*) or *Epidermophyton* or in mucosal infections caused by *Candida albicans* (e.g. thrush and vaginal candidiasis). They may also be used in the treatment of systemic fungal infections caused by, for example *Candida albicans, Cryptococcus neoformans, Aspergillus fumigatus, Coccidiodes, Paracocciciodes, Histoplasma* or *Blastomyces* spp. They may also be of use in treating eumycotic mycetoma, chromoblastomycosis and phycomycosis. Other fungal infections for which compounds of this invention are applicable and considerable background information on assays for comparative evaluation of the compounds, formulation and administration of rapalogs for treating fungal infection can be found in Holt et al, U.S. Pat. No. 6,258,823 (issued Jul. 10, 2001) and references cited therein. Note that antifungal rapalogs of this invention may retain the methoxyl substituent at C7 or may contain any of a variety of replacement substituents, including H and bulky or non-bulky substituents. U.S. Pat. No. 6,258,823, for instance, discloses a series of C7 replacement substituents which may be incorporated into the design of compounds of Figure I, especially for antifungal or multimerizing applications.

Compounds of this invention may also be used to treat primary and/or metastatic cancers. They should be useful for reducing tumor size, inhibiting tumor growth or metastasis; treating pain associated with bone cancers; and treating and/or prolonging the survival time of animals or patients with those diseases.

Accordingly this invention provides compounds for use in medical therapy, in particular for use as antifungal, anticancer, immunosuppressive or anti-restenotic agents, or as agents against the other diseases and conditions disclosed herein.

The invention further provides a method of treating a human or non-human animal suffering from any of those diseases or conditions by the administration of an effective amount of the rapalog, and further provides pharmaceutical compositions comprising a compound of the invention together with a pharmaceutically acceptable diluent or carrier, as well as medical devices, such as drug-bearing stents, containing a compound of this invention.

Compounds of this invention may be formulated as disclosed below and elsewhere herein (or using formulations based on those reported for rapamycin or rapamycin derivatives such as AP23573, CCI-779 or RAD001), and may then be administered in treatment effective amounts to patients in need thereof for the treatment of a variety of diseases as noted herein. Such compositions may be administered in any manner useful in directing the active compounds to the recipient's bloodstream or site of action, including orally, parenterally (including intravenous, intraperitoneal and subcutaneous injections as well as injection into joints or other tissues), via stents or other implants, rectally, intranasally, vaginally, and transdermally. For the purposes of this disclosure, transdermal administrations are understood to include all administrations across the surface of the body and the inner linings of bodily passages including epithelial and mucosal tissues. Such administration may be carried out using the present compounds, or pharmaceutically acceptable salts or prodrugs thereof, in lotions, creams, foams, patches, suspensions, solutions, and suppositories (rectal and vaginal).

For parenteral or intraperitoneal administration, solutions or suspensions of these active compounds or a pharmacologically acceptable salt thereof can be prepared in water suitably mixed with a surfactant such as hydroxy-propylcellulose or by adaptation of formulations used for rapamycin, AP23573, CCI779 or RAD001. Dispersions can also be prepared in glycerol, liquid polyethylene glycols and mixtures thereof in oils. Under ordinary conditions of storage and use, these preparations may contain a preservative to prevent the growth of microorganisms.

Compositions which contain a compound of this invention and which are suitable for injectable use include sterile aqueous solutions or dispersions and sterile powders for the extemporaneous preparation of sterile injectable solutions or dispersions. In all cases, the composition to be injected should be sterile and should be sufficiently fluid to permit transfer via syringe. It should be stable under the conditions of manufacture and storage and will preferably be protected from the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Parenteral formulations which may be adapted for use with rapalogs of this invention are disclosed in U.S. Pat. Nos. 5,530,006; 5,516,770; and 5,616,588.

Formulation, routes of administration and dosing may be selected from, or based upon, those used for rapamycin and other rapalogs used for the same or analogous indications. For treating tumors, it may be preferred to first determine whether the function of PTEN (or PTEN-mediated processes) is partially or wholly deficient in a patient's tumor, and then to selectively treat the patients with PTEN-deficient tumors (See e.g., Neshat et al, PNAS, above). More generally, a preferred approach may be to determine through genotype analysis and/or in vitro culture and study of biopsied tumor samples, those patients with tumors in which the phosphatidyl-inositol 3 ("PI3") kinase/Akt-mTOR signaling pathway is particular important to cell growth, and then to selectively treat those patients with rapalog. Non-limiting examples of such cancers involving abnormalities in the PI3 kinase/Akt-mTOR pathway include glioma, lymphoma and tumors of the lung, bladder, ovary, endometrium, prostate or cervix which are associated with abnormal growth factor receptors (e.g. EGFR, PDGFR, IGF-R and IL-2); ovarian tumors which are associated with abnormalities in PI3 kinase; melanoma and tumors of the breast, prostate or endometrium which are associated with abnormalities in PTEN; breast, gastric, ovarian, pancreatic, and prostate cancers associated with abnormalities with Akt; lymphoma, cancers of the breast or bladder and head and neck carcinoma associated with abnormalities in eIF-4E; mantle cell lymphoma; breast cancer and head and neck carcinomas associated with abnormalities in Cyclin D; and familial melanoma and pancreas carcinomas associated with abnormalities in P16.

For all of the indications noted herein, it may be beneficial in some cases to treat the patient with a combination of a compound of this invention and one or more other agents useful for treating the relevant disease. The combination may be administered together or separately (e.g., serially). For instance, a patient being treated with an anti-cancer compound of this invention, may (before, during or after such treatment) also be treated with one or more other anti-cancer agents such as cisplatin; an antiestrogen (e.g., raloxifene, droloxifene, idoxifine, nafoxidine, toremifene, TAT-59, levomeloxifene, LY-353381, CP-3361656, MDL-103323, EM-800 and ICI-182,780; see e.g. WO 02/13802 which may be adapted to the present invention); an inhibitor of a kinase such as Src, BRC/Abl, kdr, aurora-2, glycogen synthase kinase 3 ("GSK-3"), cKit, an epidermal growth factor receptor ("EGF-R"), or platelet derived growth factor receptor ("PDGF-R") for example, including inhibitors such as Gleevec, Iressa, CP-358774 (Tarceva), ZD-1839, SU-5416, SU11248, or NSC-649890; an antibody (such as Herceptin) to a receptor or hormone (e.g. VEGF or her2) implicated in a cancer, or a soluble receptor or other receptor antagonist to such receptor; a proteasome inhibitor such as Velcade; an IKK inhibitor or other NF-kB inhibitor; or radiation. Each component of the combination may be administered as it would be if given alone, although in some cases reduced dosing of one or more components may be possible or beneficial in view of the combined action of the different drugs.

Compounds of this invention can also be administered systemically or locally or on devices such as stents, as described in PCT/US03030 to prevent reocclusion.

Further discussion of pharmaceutical uses, formulation, dosing, and administration is provided below.

DETAILED DESCRIPTION OF THE INVENTION

In reading this document, the following information and definitions apply unless otherwise indicated. In addition, unless otherwise indicated, all occurrences of a functional group are independently chosen, as the reader is in some cases reminded by the use of a slash mark or prime to indicate simply that the two occurrences may be the same or different (e.g., R and R'). Numbering of atoms in or relating to chemical structures disclosed in this document is with reference to the numbering system shown in Formula I. Also, the reader is directed to pages 15-18 of WO 01/14387 for additional definitions and orienting information which supplement the following.

The term "aliphatic" as used herein includes both saturated and unsaturated (but non-aromatic), straight chain (i.e., unbranched), branched, cyclic, or polycyclic non-aromatic hydrocarbon moieties, which are optionally substituted with one or more functional groups. Unless otherwise specified, alkyl, other aliphatic, alkoxy and acyl groups preferably contain 1-8 (i.e., "C1-C8" or "$C_{1-8}$"), and in many cases 1-6 (i.e., "C1-C6"), contiguous aliphatic carbon atoms. Illustrative aliphatic groups thus include, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents.

The term "aliphatic" is thus intended to include alkyl, alkenyl, alkynyl, cycloalkyl, cycloalkenyl, and cycloalkynyl moieties.

As used herein, the term "alkyl" includes both straight, branched and cyclic alkyl groups. An analogous convention applies to other generic terms such as "alkenyl", "alkynyl" and the like. Furthermore, as used herein, the language "alkyl", "alkenyl", "alkynyl" and the like encompasses both substituted and unsubstituted groups.

The term "alkyl" refers to groups usually having one to eight, preferably one to six carbon atoms. For example, "alkyl" may refer to methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, and the like. Suitable substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl and the like.

The term "alkenyl" refers to groups usually having two to eight, preferably two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. The language "alkynyl," which also refers to groups having two to eight, preferably two to six carbons, includes, but is not limited to, prop-2-ynyl, but-2-ynyl, but-3-ynyl, pent-2-ynyl, 3-methylpent-4-ynyl, hex-2-ynyl, hex-5-ynyl, and the like.

The term "cycloalkyl" as used herein refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic or heteroaliphatic or heterocyclic moieties, may optionally be substituted.

The term "acyl" refers to groups of from one to eight carbon atoms of a straight, branched, cyclic configuration, saturated, unsaturated and aromatic and combination thereof, attached to a parent structure through a carbonyl functionality. One or more carbons in the acyl residue may be replaced by a nitrogen, oxygen, or sulfur as long as the point of attachment to the parent remains at the carbonyl. Examples include acetyl, benzoyl, propionyl, isobutyryl, t-butoxycarbonyl, benzyloxycarbonyl and the like.

The term "heteroaliphatic" as used herein refers to aliphatic moieties which contain one or more oxygen, sulfur, nitrogen, phosphorous or silicon atoms, e.g., in place of carbon atoms. Heteroaliphatic moieties may be branched, unbranched or cyclic and include heterocycles such as morpholino, pyrrolidinyl, etc.

The term "heterocycle", "heterocyclyl", or "heterocyclic" as used herein refers to non-aromatic ring systems having five to fourteen members, preferably five to ten, in which one or more ring carbons, preferably one to four, are each replaced by a heteroatom such as N, O, or S. Non-limiting examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "aryl" used alone or as part of a larger moiety as in "aralkyl", "aralkoxy", or "aryloxyalkyl", refers to aromatic ring groups having five to fourteen ring members, such as phenyl, 1-naphthyl, 2-naphthyl, 1-anthracyl and 2-anthracyl.

The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Non-limiting examples of useful aryl ring groups include phenyl, halophenyl, alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "heteroaryl" as used herein refers to stable heterocyclic, and polyheterocyclic aromatic moieties having 3-14, usually 5-14, carbon atoms, which moieties may be substituted or unsubstituted and may comprise one or more rings. Substituents include any of the previously mentioned substituents. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). Further specific examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisoxazolyl. Heteroaryl groups further include a group in which a heteroaromatic ring is fused to one or more aromatic or nonaromatic rings where the radical or point of attachment is on the heteroaromatic ring. Examples include tetrahydroquinoline, tetrahydroisoquinoline, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl group (including the aryl portion of an aralkyl, aralkoxy, or aryloxyalkyl moiety and the like) or heteroaryl group (including the heteroaryl portion of a heteroaralkyl or heteroarylalkoxy moiety and the like) may contain one or more substituents. Examples of suitable substituents on the unsaturated carbon atom of an aryl or heteroaryl group include halogen, trihaloalkyl, —$YR^2$, —Y—C(=O)$R^2$, —Y—C(=O)O$R^2$, —Y—C(=O)N$R^2R^5$, —Y—C(=N$R^2$)N$R^2R^5$, (in which Y is a bond, —O—, —S—. N$R^5$), —COCO$R^2$, —COMCO$R^2$ (in which M is substituted or unsubstituted methylene moiety), J, —CN, —S(=O)$R^2$, —SO$_2R^2$, —SO$_2$N$R^2R^5$, —NO$_2$, —N$R^5$SO$_2R^2$, OSO$_2R^2$, and N$R^5$SO$_2$N$R^2R^5$. To illustrate further, substituents in which Y is $NR^5$ thus include among others, $-NR^5C(=O)R^2$, $-NR^5C(=O)NR^2$, $-NR^5C(=O)OR^2$, and $-NR^5C(=NH)NR^2$. $R^2$ and $R^5$ substituents are selected from Hydrogen, an aliphatic, a heteroaliphatic, an aryl and a heteroaryl. $R^2$ and $R^5$ may themselves be substituted or unsubstituted (e.g. non-limiting illustrations of an $R^5$ moiety include -alkylhalo such as chloromethyl or trichloromethyl; -alkoxyalkyl such as methoxyethyl-; mono-, di- and tri-alkoxyphenyl; methylenedioxyphenyl or ethylenedioxyphenyl; halophenyl; and alkylamino). Additional illustrative examples include 1,2-methylene-dioxy, 1,2-ethylenedioxy, protected OH (such as acyloxy)), phenyl, substituted phenyl, —O-phenyl, —O-(substituted) phenyl, -benzyl, substituted benzyl, —O-phenethyl (i.e., $-OCH_2CH_2C_6H_5$), —O-(substituted) phenethyl, $-C(O)CH_2C(O)R^2$, $-CO_2R^2$, $-C(=O)R^2$ (i.e., acyl in cases in which $R^2$ is aliphatic, aroyl in cases in which $R^2$ is aryl and heteroaroyl in cases in which $R^2$ is heteroaryl), $-C(=O)NR^2R^5$, $-OC(=O)NR^2R^5$, $-C(=NH)NR^2R^5$, and $-OC(=NH)NR^2R^5$. Further examples of substituents include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl groups.

An aliphatic, heteroaliphatic or non-aromatic heterocyclic group may also contain one or more substituents. Examples of suitable substituents on such groups include those listed above for the carbon atoms of an aryl or heteroaryl group and in addition include the following substituents for a saturated carbon atom: halo, trihaloalkyl, $SO_2-CF_3$, $OSO_2F$, $OSO_2R_2$, CHO, $CO_2H$ (or ester, carbamate, urea, oxime or carbonate thereof), aryl or heteroaryl, $=O$, $=S$, $=NR^2$, $=NNR^2R^5$, $=NNHC(O)R^2$, $=NNHCO_2R^2$, or $=NNHSO_2R^2$. Illustrative examples of substituents on an aliphatic, heteroaliphatic or heterocyclic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl groups.

Illustrative substituents on the nitrogen of an aromatic or non-aromatic heterocyclic ring include $-R^2$, $-NR^2R^5$, $-C(=O)R^2$, $-C(=O)OR^2$, $-C(=O)NR^2R^5$, $-C(=NR^2)NR^2R^5$, $-COCOR^2$, $-COMCOR^2$), $-CN$, $-SO^2R^2$ and $-SO_2NR^2R^5$.

Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkoxycarbonyloxy, alkylcarbonyl, alkycarbonyloxy, hydroxy, haloalkoxy, or haloalkyl.

A combination of substituents or variables is permissible only if such a combination results in a stable or chemically feasible compound. For the purposes of this document, a stable compound or chemically feasible compound is one that is not substantially altered when kept at a temperature of 40° C. or less, in the absence of moisture or other chemically reactive conditions, for at least a week.

Certain compounds of this invention may exist in tautomeric forms, and this invention includes all such tautomeric forms of those compounds unless otherwise specified.

Unless a particular stereochemistry is specified verbally or graphically, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Thus, this invention encompasses each diasteriomer or enantiomer substantially free of other isomers (>90%, and preferably >95%, free from other stereoisomers on a molar basis) as well as a mixture of such isomers. (In chemical structures in this document, a simple line, e.g. the line in Formula I to the substituents at positions 43 and 28, indicates either R or S orientation.) A reference to an "altered" stereochemistry indicates a stereochemistry other than that found at the corresponding site in rapamycin itself.

Unless otherwise stated, structures depicted herein are also meant to include compounds which differ only in the presence of an alternative isotope for one or more atoms. For example, compounds having the present structures except for the replacement of a hydrogen by a deuterium or tritium, or the replacement of one or more $^{12}C$ atoms by a $^{13}C$ or $^{14}C$ atom are within the scope of this invention.

A JQA-containing rapalog as described herein (i.e., 43-JQA-C(O)O-containing rapalogs) may differ from the corresponding 43-JQA-containing derivative of rapamycin with respect to zero, one, two, three, four, five, six or seven (or more) substituent moieties or functional groups at positions other than position 43. One class of rapalogs of this invention includes JQA-containing rapalogs with no other modifications, relative to rapamycin, i.e., other than the JQA modification at position 43. Another class includes among others JQA-containing rapalogs with additional modification(s) at any one, two, three, four, five or all six of positions C7, C13, C14, C24, C28 and C30. Modifications in rapalog structure are known for a number of previously known rapalogs (see e.g. WO 99/36553, Table III and Liberles et al, 1997, *Proc Natl Acad Sci USA* 94:7825-7830 and infra) and may be readily adapted to the present invention. See also WO 01/14387, including among others pages 24-30, for information on known modifications and combinations of modifications known for rapamycin which may be used in the design of JQA-containing rapalogs.

One subset of JQA-containing rapalogs of special interest for practicing the methods of this invention are those (or pharmaceutically acceptable derivatives thereof) in which $R^{7a}$ is a moiety other than OMe. This subset ("JQA-containing C7 rapalogs") includes compounds in which one of $R^{7a}$ and $R^{7b}$ is H and the other is selected from $-R^A$, $-Z-R^A$, $-Z-(CO)R^A$, $-Z-(CO)ZR^A$, $-NR^ASO_2R^A$ and $-NR^ASO_2R^A$, where each Z is independently O, S or $NR^B$. Illustrating this subset are the JQA-containing rapalogs bearing a C7 substituent selected from the following group: aryl; heteroaryl; aryl, heteroaryl or benzyl ether; and $-NH(CO)OR^A$, $-NH(CO)R^A$, $-NH(SO_2)R^A$ or $-NH(SO_2)NHR^A$ (where $R^A$ is selected from H, an aliphatic, a heteroaliphatic, an aryl and an heteroaryl moiety and $R^B$ is selected from H, OH, an aliphatic, a heteroaliphatic, an aryl and an heteroaryl moiety). Examples of $R^A$ and $R^B$ are a substituted or unsubstituted lower alkyl, e.g., methyl, ethyl, iPr, butyl, benzyl, etc. or is a substituted or unsubstituted phenyl (e.g., p-tolyl); In certain embodiments of this subset, $R^{7a}$ and $R^{7b}$ are independently selected from the following groups: H; a substituted or unsubstituted two to eight carbon straight chain, branched or cyclic alkenyl, alkoxyl or alkylmercapto; and a substituted or unsubstituted aryl, heteroaryl, aryloxy or heteroaryloxy, arylmercapto or heteroarylmercapto. Compounds of this subset include among others those in which $R^{7a}$ is H; (together with $R^{7b}$) =O; alkoxy; alkylmercapto; amino (primary, secondary, tertiary or quaternary); amido; carbamate; aryl or substituted aryl; phenyl or substituted phenyl; substituted or unsubstituted heteroaryl such as substituted or unsubstituted thiophenyl, furyl, indolyl, etc.; or benzyloxy or substituted benzyloxy. Other illustrative JQA-containing C7 rapalogs which may be used in practicing the methods of this invention include those in which one of $R^{7a}$ and $R^{7b}$ is H and the other is selected from —OEt, —O-propyl, —O-butyl, —OCH$_2$CH$_2$—OH, —O-benzyl, —O-substituted benzyl (including e.g., 3-nitro-, 4-chloro-, 3-iodo-4-diazo-, 3,4-dimethoxy-, and 2-methoxy-), —S-Me, —S-phenyl, —O(CO)Me, -allyl, —CH$_2$C(Me)=CH$_2$, —OCH$_2$—CCH, —OCH$_2$—CC-Me, —OCH$_2$—CC-Et, —OCH$_2$—CC—CH$_2$OH, or -2,4-dimethoxyphenyl, 2,4,6-trimethoxyphenyl, furanyl, thiophen-yl, methylthiophen-yl, pyrolyl and indolyl. C7-modified JQA-containing rapalogs of particular interest are those bearing a substituted or unsubstituted aromatic ether, a substituted or unsubstituted benzyl ether or a carbamate moiety at C7. In C7-modified embodiments, the substituent at C43 may be present in either stereochemical orientation (or as a mixture of isomers). JQA-containing C7 rapalogs may further vary from the corresponding C7-modified rapamycin at one, two, three, four, five or more other positions as well.

43 JQA-rapamycin and JQA-containing C7 rapalogs of are of particular interest.

Another subset of JQA-containing rapalogs of special interest in the practice of the various methods of the invention are those in which the substituents at C24 and C30 are both other than (=O). Of special interest are those C30 and C24 substituents disclosed in WO 99/36553. This subset includes among others all 43-JQA-containing rapalogs in which $R^{C30}$ and $R^{C24}$ are OH and one of $R^{C7a}$ and $R^{C7b}$ comprises any of the replacement substituents at that position specified herein, including any of the C7 substituents identified in WO 01/14387. Of special interest are compounds in which one of $R^{C7a}$ and $R^{C7b}$ is cyclic aliphatic, aryl, heterocyclic or heteroaryl, which may be optionally substituted. Other compounds within this subset include those in which one, two, three, four or five of the hydroxyl groups is epimerized, fluorinated, alkylated, acylated or otherwise modified via other ester, carbamate, carbonate or urea formation. An illustrative compound for example is the JQA-containing rapalog in which the hydroxyl groups at C28 and C30 are alkylated, acylated or linked via carbonate formation.

Another subset of JQA-containing rapalogs of special interest are the mono- and difluoro-JQA-containing rapalogs which contain an F at one or both of C13 and C28, as disclosed in WO 99/36553, with or without additional changes elsewhere in the JQA-containing rapalog molecule.

Another subset of JQA-containing rapalogs of interest have an $R^{C24}$ which is other than =O, again, with or without one or more other modifications at other positions relative to rapamycin.

Other JQA-containing rapalogs of interest include those in which $R^{C14}$ is OH.

Furthermore, this invention encompasses JQA-containing rapalogs in which one or more of the carbon-carbon double bonds at the 1,2, 3,4 or 5,6 positions in rapamycin are saturated, alone or in combination with a modification elsewhere in the molecule, e.g. at one or more of C7, C13, C24 C28 and/or C30. It should also be appreciated that the C3,C4 double bond may be epoxidized; that the C6 methyl group may be replaced with —CH$_2$OH or —CH$_2$OMe; that the C42 methoxy moiety may be demethylated, in any of the compounds disclosed herein, using methods known in the art.

Additional Guidance on Techniques for Preparation and Use

The production of rapamycin by fermentation and by total synthesis is known. The production of a number of rapalogs as fermentation products is also known. These include among others rapalogs bearing alternative moieties in place of the characteristic cyclohexyl ring or pipecolate ring of rapamycin, as well as C7-desmethyl-rapamycin, C29-desmethyl-rapamycin and C29-desmethoxyrapamycin, among others.

Methods and materials for effecting various chemical transformations of rapamycin and structurally related macrolides are known in the art. Many such chemical transformations of rapamycin and various rapalogs are disclosed in the patent documents identified in Table I of WO/014387 which help illustrate the level of skill and knowledge in the art of chemical synthesis and product recovery, purification and formulation which may be applied in practicing the subject invention. Also see, e.g., the following patent documents for additional synthetic background:

| | |
|---|---|
| US Pat. No. 4316885 | Acyl derivatives of rapamycin |
| US Pat. No. 5023262 | Hydrogenated rapamycin derivatives |
| US Pat. No. 5023263 | 42-oxorapamycin |
| US Pat. No. 5023264 | Rapamycin oximes |
| US Pat. No. 5100883 | Fluorinated esters of rapamycin |
| US Pat. No. 5102876 | Reduction products of rapamycin |
| US Pat. No. 5118677 | Amide esters of rapamycin |
| US Pat. No. 5118678 | Carbamates of rapamycin |
| US Pat. No. 5120726 | Rapamycin hydrazones |
| US Pat. No. 5130307 | Aminoesters of rapamycin |
| US Pat. No. 5162333 | Aminodiesters of rapamycin |
| US Pat. No. 5221670 | Rapamycin esters |
| US Pat. No. 5233036 | Rapamycin alkoxyesters |
| US Pat. No. 5378696 | Rapamycin esters |
| US Pat. No. 5776943 | Rapamycin metabolites |
| WO 92/05179A1 | Carboxylic Acid Esters Of Rapamycin |
| WO 93/05046A1 | Aminodiesters Of Rapamycin |

A wide variety of bisphosphonates (alendronate, pamidronate, etc.) are known and are commercially available or readily synthesized which may be used in the practice of this invention, i.e., which may be coupled to rapamycin or a rapalog to produce some of the compounds of this invention. Likewise, a variety of (HO)$_2$P(=O)CH$_2$P(=O)(OH)-containing compounds are known and readily synthesized (see e.g., WO 01/44259) for coupling to rapamycin or a rapalog to produce other of the compounds of this invention. Methods and materials for activating, protecting/deprotecting and coupling the starting materials are also well known and are illustrated in the examples which follow.

See also WO 03/064383, USSN 2005/0032825 and WO 2005/016252 for additional guidance on synthesis, physicochemical characterization, biological characterization and use of other rapalogs. A variety of biochemical and cell-based methods are known in the art for characterizing biological activity of these compounds, e.g., measuring binding affinity to FKBP (see e.g., Sierkierka et al, 1989, Nature 341, 755-757; WO 99/36553 and WO 96/41865), inhibition of cell proliferation, etc. One may also measure the effect of these compounds on any of the pharmacodynamic markers of mTOR inhibitory activity, a variety of which are known in the art, as well as the effect of these compounds on inhibition of bone resorption in an animal model of osteoporosis, including for example, an ovariectomized rodent model. Compounds of this invention, especially those in which one or more hydroxyl groups of the phosphonate and/or phosphinate moieties are not further derivatized, may also be characterized using conventional materials and methods to assess their binding affinity for hydroxyapatite to provide an indication of a compound's affinity for bone. For prodrugs and other derivatives of phosphonates, phosphinates and related moieties, see Atack et al, J of Pharmacology and Experimental Therapeutics 1994, 270, 70; Arimilli et al, Antiviral Chem & Chemotherapy 1997, 8, 557; Serafinowska et al, J Med Chem, 1995, 35, 1372; Ahlmark, J Med Chem, 1999, 42, 1473; Meier et al, J Med Chem, 1998, 41, 1417; Krise et al, Advanced Drug Delivery Reviews 1996, 19, 287 and references cited therein, as well as WO 01/44259

Applications

In addition to applications and drug combinations noted in PCT/US03/03030 and U.S. Ser. No. 10/357,152 and references cited therein, certain compounds of the invention will be of interest for their use in treating bone cancers and for their ability to inhibit osteoclast function, and may be useful in treating patients with debilitating bone disorders such as osteoporosis, particularly osteoporosis associated with the peri and post menopausal conditions. A compound of this invention may also be administered to patients who have, or are at risk of, Paget's disease, hypercalcemia associated with bone neoplasms and other types of osteoporotic diseases and related disorders, including but not limited to involutional osteoporosis, Type I or postmenopausal osteoporosis, Type II or senile osteoporosis, juvenile osteoporosis, idiopathic osteoporosis, endocrine abnormality, hyperthyroidism, hypogonadism, ovarian agensis or Turner's syndrome, hyperadrenocorticism or Cushing's syndrome, hyperparathyroidism, bone marrow abnormalities, multiple myeloma and related disorders, systemic mastocytosis, disseminated carcinoma, Gaucher's disease, connective tissue abnormalities, osteogenesis imperfecta, homocystinuria, Ehlers-Danlos syndrome, Marfan's syndrome, Menke's syndrome, immobilization or weightlessness, Sudeck's atrophy, chronic obstructive pulmonary disease, chronic heparin administration, and chronic ingestion of anticonvulsant drugs.

Several of these uses are further discussed below.

Pharmaceutical Uses

Compounds of this invention are of interest as antineoplastic agents, especially for treatment of bone cancers. In particular, the compounds of this invention may be used alone or in combination with other drugs and/or radiation therapy in treating or inhibiting the growth of such cancers. Their use is analogous to that of rapamycin or CCI779 as disclosed in Sorbera et al, "CCI-779" Drugs of the Future 2002, 27(1):7-13; WO 02/4000 and WO 02/13802, for example. Examples of other drugs that can be used to treat cancer patients in conjunction with (i.e., before, during or after administration of a compound of this invention) a compound of this invention include, among others, Zyloprim, alemtuzmab, altretamine, amifostine, nastrozole, antibodies against prostate-specific membrane antigen (such as MLN-591, MLN591RL and MLN2704), arsenic trioxide, Avastin® (or other anti-VEGF antibody), bexarotene, bleomycin, busulfan, capecitabine, carboplatin, Gliadel Wafer, celecoxib, chlorambucil, cisplatin, cisplatin-epinephrine gel, cladribine, cytarabine liposomal, daunorubicin liposomal, daunorubicin, daunomycin, dexrazoxane, docetaxel, doxorubicin, Elliott's B Solution, epirubicin, estramustine, etoposide phosphate, etoposide, VP-16, exemestane, fludarabine, 5-FU, fulvestrant, gemcitabine, gemtuzumab-ozogamicin, goserelin acetate, hydroxyurea, idarubicin, idarubicin, Idamycin, ifosfamide, imatinib mesylate, irinotecan (or other topoisomerase inhibitor, including antibodies such as MLN576 (XR11576)), letrozole, leucovorin, leucovorin levamisole, liposomal daunorubicin, melphalan, L-PAM, mesna, methotrexate, methoxsalen, mitomycin C, mitoxantrone, MLN518 or MLN608 (or other inhibitors of the flt-3 receptor tyrosine kinase, PDFG-R or c-kit), itoxantrone, paclitaxel, Pegademase, pentostatin, porfimer sodium, Rituximab (RITUXAN®), talc, tamoxifen, temozolamide, teniposide, VM-26, topotecan, toremifene, Trastuzumab (Herceptin®, or other anti-Her2 antibody), 2C4 (or other antibody which interferes with HER2-mediated signaling), tretinoin, ATRA, valrubicin, vinorelbine, or pamidronate, zoledronate or another bisphosphonate.

Formulations, Pharmaceutical Compositions, Dosage and Administration

The rapalogs of this invention can exist in free form or, where appropriate, in salt form. Pharmaceutically acceptable salts of many types of compounds and their preparation are well-known to those of skill in the art. Pharmaceutically acceptable salts include conventional non-toxic salts including the quaternary ammonium salts of formed by such compounds with inorganic or organic acids of bases.

Our compounds may form hydrated species when lyophilized with water, or form solvated species when concentrated in a solution with an appropriate organic solvent.

This invention encompasses pharmaceutical compositions comprising a therapeutically (or prophylactically) effective amount of a compound of the invention, and one or more pharmaceutically acceptable carriers and/or other excipients. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation. In another approach, the composition may be formulated into nanoparticles.

The pharmaceutical carrier employed may be, for example, either a solid or liquid.

Illustrative solid carriers include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be administered by, for example, intravenous, intramuscular, intraperitoneal or subcutaneous injection. Injection may be via a single push or by gradual infusion, e.g. 30 minute intravenous infusion. The compound can also be administered orally either in liquid or solid composition form.

The carrier or excipient may include a time delay material, examples of which are well known to the art, such as glyceryl monostearate or glyceryl distearate, and may further include a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) has been recognized as providing an acceptable oral formulation for other compounds, and may be adapted to formulations for various compounds of this invention.

A wide variety of pharmaceutical forms can thus be employed in administering compounds of this invention. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, the compound, or a pharmaceutically acceptable salt thereof, may be dissolved in an aqueous solution of an organic or inorganic acid, such as a 0.3M solution of succinic acid or citric acid. Alternatively, acidic derivatives can be dissolved in suitable basic solutions. If a soluble form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0-60% of the total volume.

Various delivery systems are known and can be used to administer the compound, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes. The compound may be administered by any convenient or otherwise appropriate route, for example by infusion or bolus injection, by absorption through epithelial or mucocutaneous linings (e.g., oral mucosa, rectal and intestinal mucosa, etc.) or via a drug-loaded stent and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In certain embodiments, it may be desirable to administer the compound locally to an area in need of treatment; this may be achieved by, for example, and not by way of limitation, local infusion during surgery, topical application, by injection, by means of a catheter, by means of a suppository, or by means of a skin patch or stent or other implant, said implant typically being of a porous, non-porous, or gelatinous material, including membranes, such as sialastic membranes, or fibers.

In a specific embodiment, the composition is formulated using routine methods as a pharmaceutical composition for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

For example, a solution of a rapalog of this invention for injection may contain 0.1 to 10 mg/ml, e.g. 1-3 mg/ml, of rapalog in a diluant solution containing Phosal 50 PG (phosphatidylcholine, propylene glycol, mono- and di-glycerides, ethanol, soy fatty acids and ascorbyl palmitate) and polysorbate 80, containing 0.5-4% ethanol, e.g. 1.5%-2.5% ethanol. As another example, the diluant may contain 2-8%, e.g. 5-6%, each of propylene glycol USP and polysorbate 80 in water for injection. We have found that 5.2% of each works well for some rapalogs. Typically a solution is processed using conventional methods and materials, including e.g. one or more rounds of sterile filteration.

Oral formulations containing a compound of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Suitable surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed. Oral formulations which may be adapted for use with rapalogs of this invention are disclosed in U.S. Pat. Nos. 5,559,121; 5,536,729; 5,989,591; 5,985,325; 5,145,684 (nanoparticles); U.S. Pat. No. 6,197,781; and WO 98/56358. Tablets containing a rapalog of this invention may contain conventional inactive ingredients including for example sucrose, lactose, polyethylene glycol 8000, calcium sulfate, microcrystalline cellulose, pharmaceutical grade glaze, talc, titanium dioxide, magnesium stearate, povidone, poloxamer 188, polyethylene glycol 20,000, glyceryl monooleate, carnauba wax, and other ingredients. Nanosized compositions for oral administration may also be used. In such cases nanoparticles are formed from compositions containing (on a weight/weight basis) 1-20% rapalog, 70-95% inert material such as sucrose, 0.1 to 4% of materials such as polyvinyl pyrrolidone and benzylconium chloride and 0-1% surfactant such as Tween. An illustrative such composition contains about 15% rapalog, 81% sucrose, 2% polyvinyl pyrrolidone, 2% benzylconium chloride and 0.1% Tween.

In some cases it may be desirable to administer the compounds directly to the airways in the form of an aerosol.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed within transdermal devices placed upon, in, or under the skin. Such devices include patches, implants, and injections which release the compound into the skin, by either passive or active release mechanisms. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

Materials and methods for producing the various formulations are known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; illustrative formulation for IV administration) and 0 648 494 (published Apr. 19, 1995; illustrative formulation for oral administration). See also U.S. Pat. No. 5,145,684 (nanoparticles) and U.S. Pat. No. 5,989,591 (solid dosage forms) and WO 98/56358 as well as Yu, K. et al., Endocrine-Related Cancer (2001) 8, 249-258 and Geoerger et al., Cancer Res. (2001) 61 1527-1532.

The effective systemic dose of the compound will typically be in the range of about 0.01 to about 100 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient. Administration may be once or multiple times daily, weekly (or at some other multiple-day interval) or on an intermittent schedule. For example, the compound may be administered one or more times per day on a weekly basis (e.g. every Monday) for a period of weeks, e.g. 4-10 weeks. Alternatively, it may be administered daily for a period of days (e.g. 2-10 days) followed by a period of days (e.g. 1-30 days) without administration of the compound, with that cycle repeated a given number of times, e.g. 4-10 cycles. As an example, an anti-cancer compound of the invention may be administered daily for 5 days, then discontinued for 9 days, then administered daily for another 5 day period, then discontinued for 9 days, and so on, repeating the cycle a total of 4-10 times.

The amount of compound which will be effective in the treatment or prevention of a particular disorder or condition will depend in part on well known factors affecting drug dosage, and in the case of gene and cell therapy applications, will also depend on the characteristics of the fusion proteins to be multimerized, the characteristics and location of the genetically engineered cells, and on the nature of the disorder or condition, which can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

When administered for the treatment or inhibition of a particular disease state or disorder, the effective dosage of the rapalog of this invention may vary depending upon the particular compound utilized, the mode of administration, the condition, and severity thereof, of the condition being treated, as well as the various physical factors related to the individual being treated. In many cases, satisfactory results may be obtained when the rapalog is administered in a daily dosage of from about 0.01 mg/kg-100 mg/kg, preferably between 0.01-25 mg/kg, and more preferably between 0.01-5 mg/kg. The projected daily dosages are expected to vary with route of administration. Thus, parenteral dosing will often be at levels of roughly 10% to 20% of oral dosing levels.

When the rapalog is used as part of a combination regimen, dosages of each of the components of the combination are administered during a desired treatment period. The components of the combination may administered at the same time; either as a unitary dosage form containing both components, or as separate dosage units; the components of the combination can also be administered at different times during a treatment period, or one may be administered as a pretreatment for the other.

The invention also provides a pharmaceutical pack or kit comprising one or more containers containing one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration. The notice or package insert may contain instructions for use of a rapalog of this invention, consistent with the disclosure herein.

The following examples contain important additional information, exemplification and guidance which can be adapted to the practice of this invention in its various embodiments and the equivalents thereof. The examples are offered by way illustration should not be construed as limiting in any way. Numerous modifications and variations of the present invention should be apparent to one of skill in the art. Such modifications and variations, including design choices in selecting, preparing, formulating and administering the rapalog of this invention; the choice of stent design, materials and methods and materials for loading the rapalog thereon and for delivery the drug-eluting stent; etc. are intended to be encompassed by the scope of the invention and of the appended claims.

Compounds of the invention, as well pharmaceutically acceptable salts, prodrugs or other derivatives thereof, may be prepared by one of ordinary skill in the art of organic chemistry using the guidance provided herein, including the Examples which follow, and the guidance provided by the references cited herein to illuminate the level of skill in the art (especially regarding chemical transformations of rapamycin and its analogs, together with additional methods, materials and background knowledge found in the readily available literature, including works such as, e.g., Reagents for Organic Synthesis, by Fieser and Fieser, John Wiley & Sons, Inc., New York, 2000; Comprehensive Organic Transformations, by Richard C. Larock, VCH Publishers, Inc., New York, 1989; the series Compendlum of Organic Synthetic Methods (1989) by Wiley-Interscience; the text Advanced Organic Chemistry, 5th edition, by Jerry March, Wiley-Interscience, New York (2001); or the Handbook of Heterocyclic Chemistry, by Alan R. Katritzky, Pergamon Press Ltd., London, (1985), to name a few. Additionally, the practitioner may find alternative methods useful for preparing our compounds in the chemical literature by searching widely available databases such as, e.g., those available from the Chemical Abstracts Service, Columbus, Ohio, or MDL Information Systems GmbH (previously Beilstein Information Systems GmbH), Frankfurt, Germany.

Preparations of these compounds may use starting materials, reagents, solvents and catalysts that are available from commercial sources or that may be readily prepared by adapting procedures in the references or resources cited above. Commercial sources of starting materials, reagents, solvents, and catalysts useful in preparing invention compounds include, for example, The Aldrich Chemical Company, and other subsidiaries of SigmaAldrich Corporation, St. Louis, Mo., BACHEM, BACHEM A.G., Switzerland, or Lancaster Synthesis Ltd., United Kingdom.

All of the scientific and patent references cited herein, including the foregoing text books, treatises and series, are hereby expressly incorporated by reference to help clarify the current state of the art.

EXAMPLES

Example 1 to Example 5 refer to compounds of this invention of Formula (I), in which Q is V.

Example 1

Alendronic Acid C-43 Rapamycin Carbamate

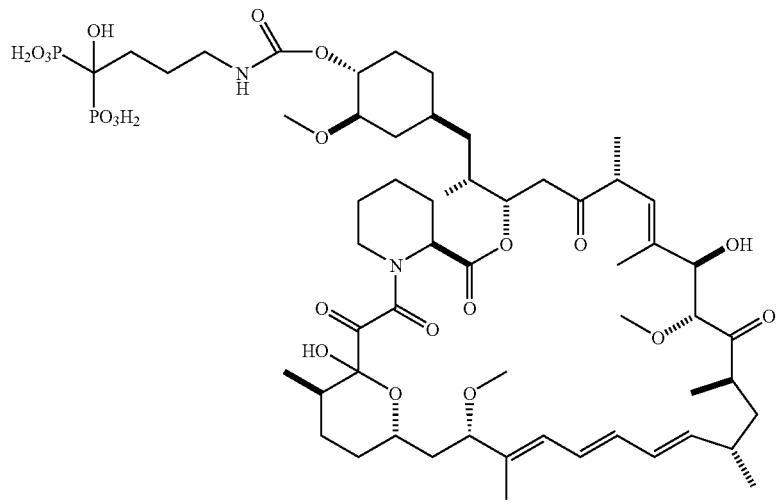

4-Nitrophenyl C-43 Rapamycin Carbonate

To a cooled (0° C.) solution of rapamycin (5.0 g, 5.47 mmol) in 80 mL of dichloromethane, under an atmosphere of $N_2$, was added a solution of 4-nitrophenyl chloroformate (1.65 g, 8.20 mmol) in 10 mL DCM, dropwise over ~1 min, followed by a solution of 3,5-lutidine (0.967 g, 9.03 mmol) in 10 mL DCM, dropwise over ~1.5 min (slight exotherms occur following each addition). The reaction solution was stirred at 0° C. for 15 min, then transferred to a separatory funnel containing EtOAc (500 mL) and saturated $NaHCO_3$ (400 mL). Upon removing the aqueous layer, the organic layer was washed successively with ice cold 1N HCl (1×400 mL), saturated $NaHCO_3$ (2×350 mL), and brine (1×350 mL), then dried over $MgSO_4$ and concentrated. The crude product was purified by silica gel flash chromatography (eluted with 1% MeOH/DCM) to provide 4.60 g of a yellow solid: 1078 m/z (M-H).

Alendronic Acid C-43 Rapamycin Carbamate

A mixture of alendronic acid (0.346 g, 1.39 mmol) and N,O-bis(trimethylsilyl)acetamide (BSA; 1.41 g, 6.95 mmol) in 4.3 mL of DMSO was heated periodically with a heat gun until all solids dissolved. Stirring at ambient temperature was continued for 1 h 15 min (cloudy, pale yellow solution results), upon which a solution of 4-nitrophenyl C-43 rapamycin carbonate (1.0 g, 0.927 mmol) in 10 mL DCM was added followed immediately by a solution of 3,5-lutidine (0.224 g, 2.09 mmol) in 2.8 mL of DCM. The resulting pale yellow reaction solution was stirred at ambient temperature for 18 h (reaction complete by TLC) then concentrated via $N_2$ flow. The concentrated yellow solution was added 11.5 mL of $H_2O$ resulting in the generation of a sticky solid (solution pH=2). The solution was decanted off and to the solid was added 25 mL acidic $H_2O$ (pH=3), resulting in a granular solid that was filtered and washed with acidic $H_2O$ (pH=3, 1×25 mL). Excess $H_2O$ was removed from the solid in a vacuum desiccator and the resulting off-white solid dissolved in 60 mL DCM, filtered (cotton plug), and the clear filtrate concentrated in vacuo. The resulting pale yellow solid was washed successively with $Et_2O$ and acidic $H_2O$ (pH=2), then dissolved in EtOAc and precipitated out of solution with hexanes to provide, following in vacuo solvent removal, 0.220 g of a pale yellow solid: $^1$H NMR (300 MHz, $CDCl_3$) δ4.98 (m, 1H), 4.94 (m, 1H), 4.37 (m, 1H), 2.92 (m, 2H); $^{31}$P NMR (121 MHz, $CDCl_3$) δ 25.5; 1188 m/z (M-H).

Example 2

Pamidronic Acid C-43 Rapamycin Carbamate

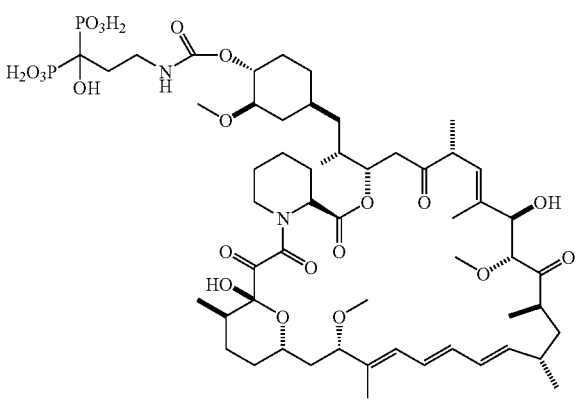

The title compound was synthesized in a manner similar to that described for Example 1. The product was obtained as a pale yellow solid: $^{31}$P NMR (121 MHz, $CDCl_3$) δ 24.9; 1174 m/z (M-H).

Example 3

Phenyl-4-phosphinoylmethyl-phosphonic Acid C-43 Rapamycin Carbamate

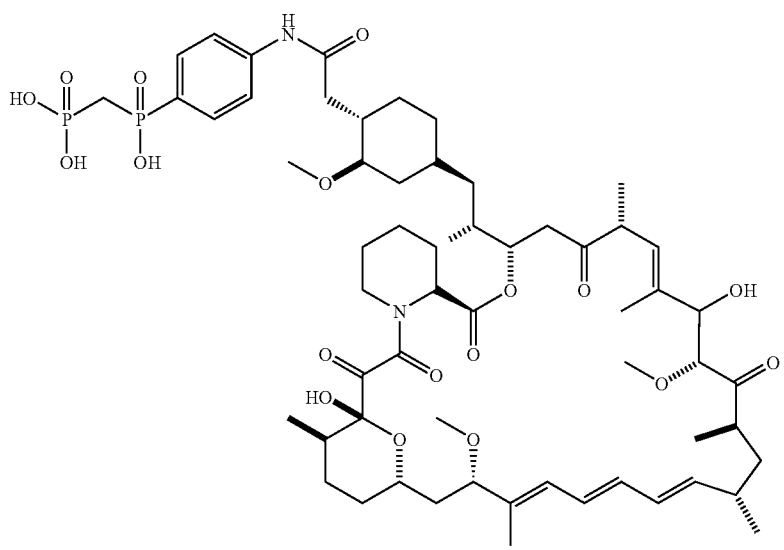

The title compound was synthesized in a manner similar to that described for Example 1, using [(4-Amino-phenyl)-phosphinoylmethyl]-phosphonic acid. The product was obtained as an off-white solid: $^{31}$P NMR (121 MHz, CDCl$_3$) δ 32.3, 20.3; 1190 m/z (M-H).

Example 4

Phenyl-4-phosphinoylmethyl-phosphonic Acid C-43 28-Epi-Rapamycin Carbamate

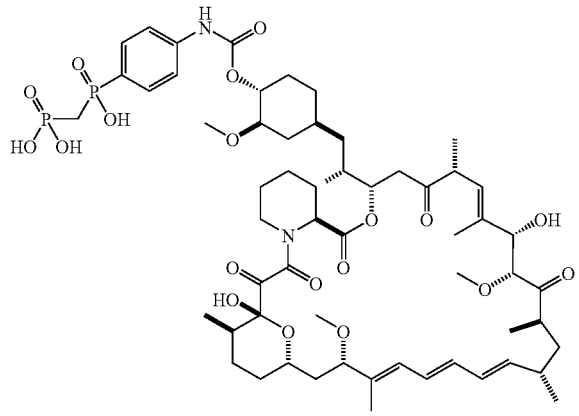

The title compound was synthesized in a manner similar to that described for Example 1, using [(4-Amino-phenyl)-phosphinoylmethyl]-phosphonic acid and 28-epi-rapamycin. The product was obtained as an off-white solid: $^{31}$P NMR (121 MHz, CDCl$_3$) δ 32.4, 20.4; 1208 m/z (M-H+ H2O).

Example 5

Synthesis Via C-43 Carbonate Activated Rapamycin

Other carbonates and carbamates of this invention may be synthesized in a manner analogous to that described for Example 1 using an activated C-43 carbonate of rapamycin (or the desired rapalog) and the desired alcohol or amine, appropriately substituted with the desired phosphonate and/or phosphinate groups, and with one or more groups, especially —OH groups, protected as appropriate.

Example 6

Alternative Synthetic Approaches Include the Following

For carbamates:

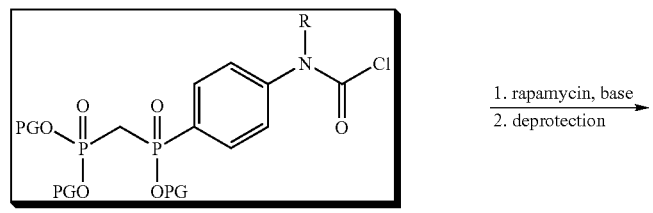

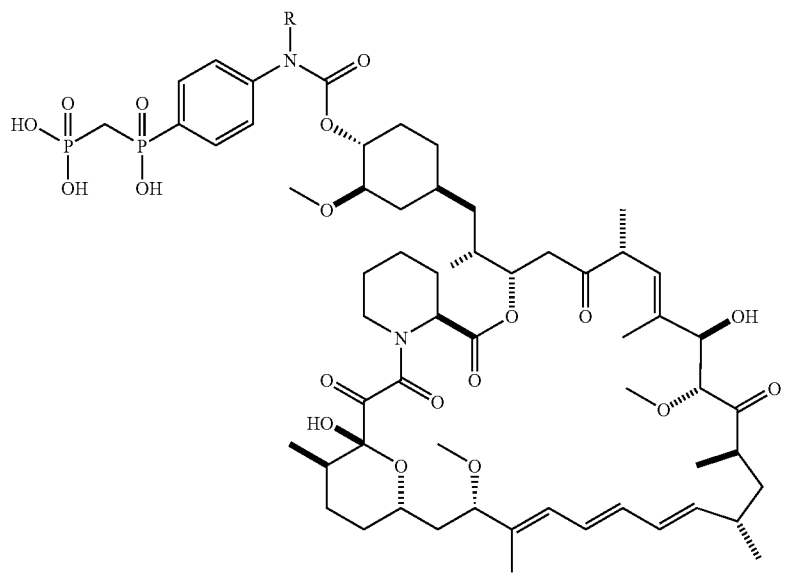

and for carbonates:

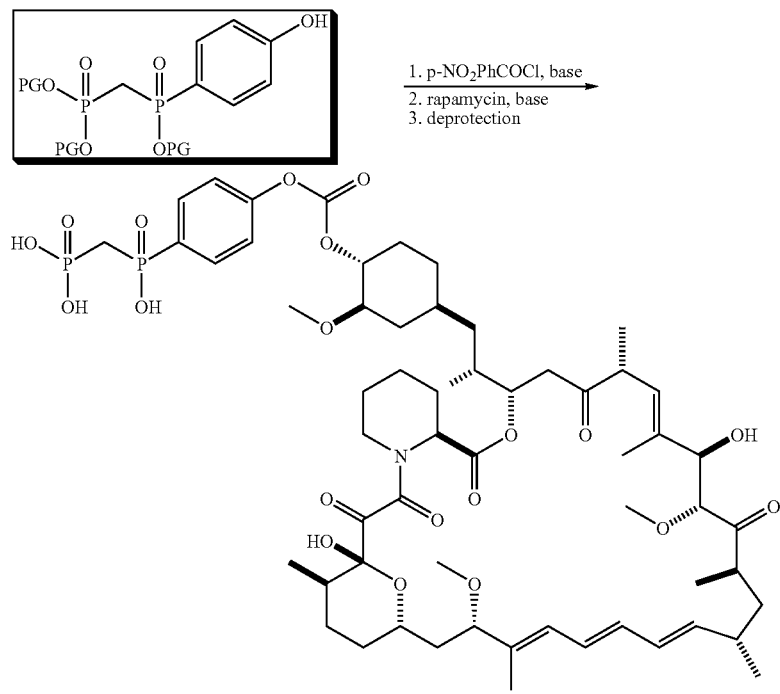

where R=H or alkyl, and PG is a protecting group. Protecting groups that can be removed under particularly mild conditions include trimethyl silyl ("TMS") ethyl-, cyanoethyl, TMS, triethyl silyl, and tri isopropyl silyl, as well as other trisubstituted silyl ethers.

The following synthetic approaches for some cyanoethyl protected intermediates may be of interest to practitioners:

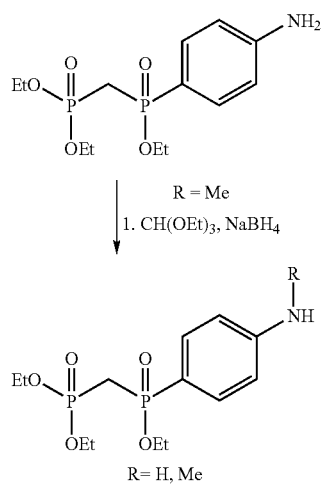

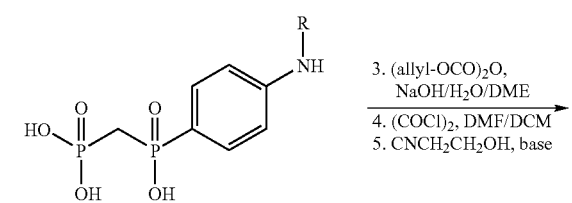

-continued

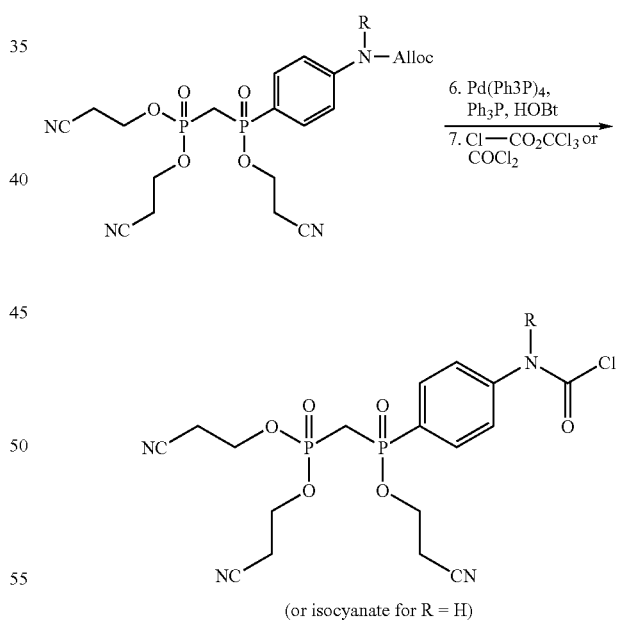

(or isocyanate for R = H)

For Step # 1 see, e.g., Heterocycles (1981), 16(9), 1491-4; for Steps #3 and 6 see, e.g., J. Comb. Chem. (2000), 2(4), 305-13; for Step #7 (R=H), see, e.g., PCT Int. Appl. 8702357, 23 Apr. 1987; J. Med. Chem. (1987), 30(7), 1166-76 and J. Med. Chem. (1987), 30(1), 62-7. For Step #7 (R=Me), see, e.g., J. Org. Chem. (1983), 48(24), -and-
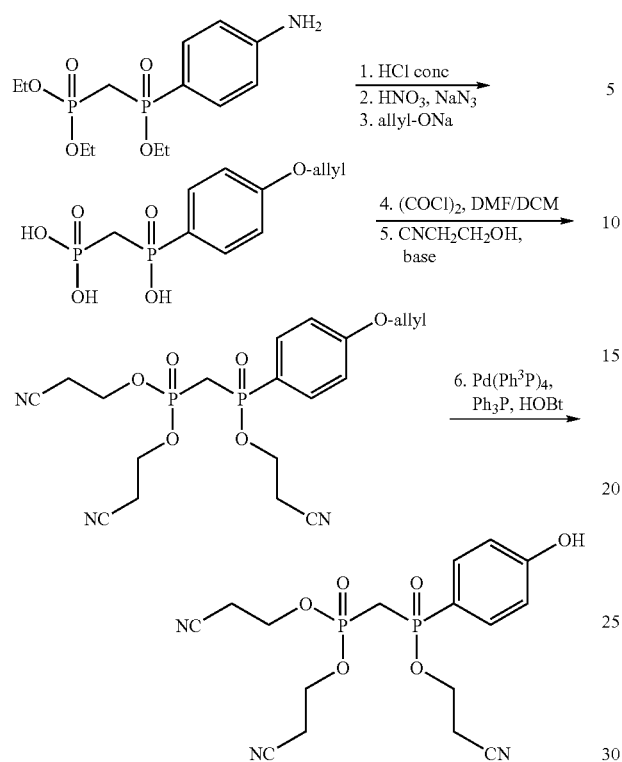
For Step # 2, see e.g., Austr. J. Chem. (1990), 43(6), 997-1007; for Step #3 see e.g., Chem Reviews (1954), 54, 1-57; and for Step #6 see e.g., J. Comb. Chem. (2000), 2(4), 305-13.
Example 6 to Example 9 refer to the compounds of the invention of Formula (I), in which Q is VN(R)V.
Example 6
Scheme for (4-(methyl(2-(methylamino)ethyl)amino)phenyl)methylenediphosphonic acid
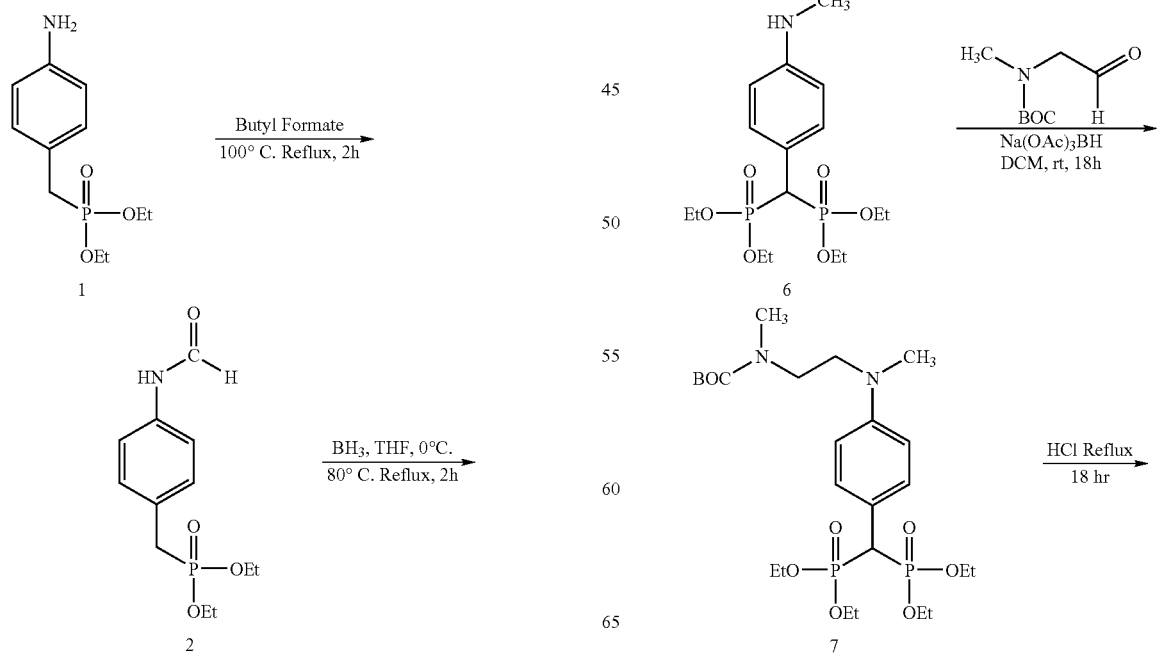
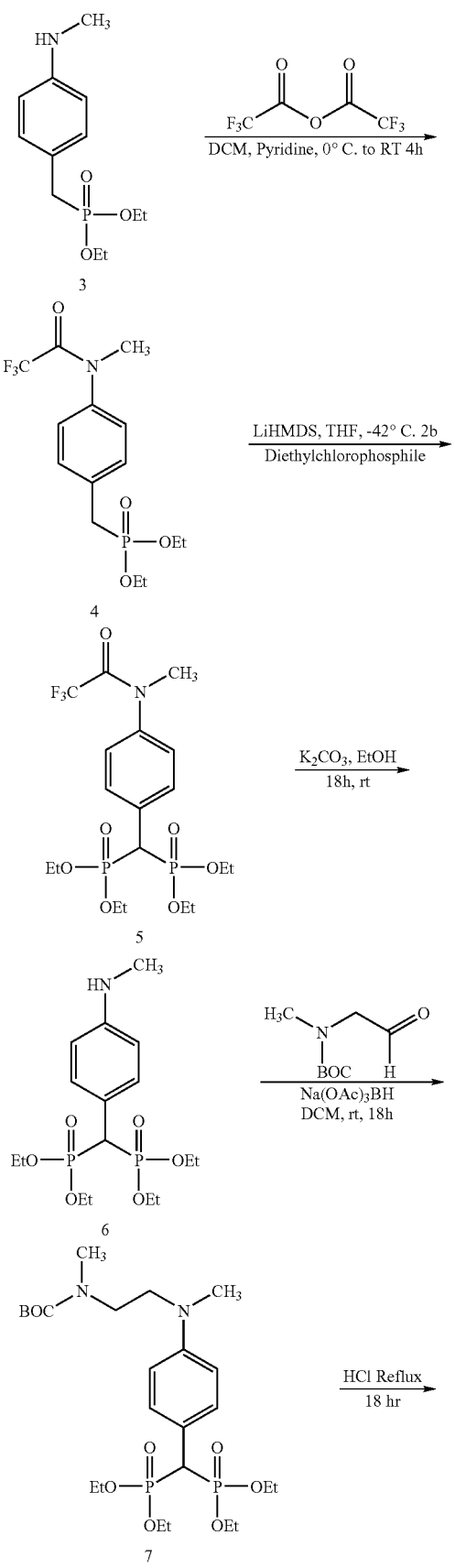

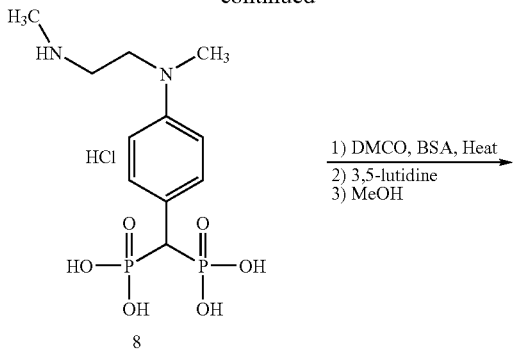

(4-(Methyl(2-(methylamino)ethyl)amino)phenyl)
methylenediphosphonic acid

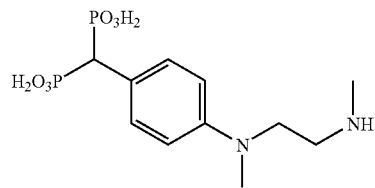

tert-Butyl methyl(2-oxoethyl)carbamate

A mixture of 2-(methylamino)ethanol (15.0 mL, 187.7 mmol), 130 mL (932.7 mmol) of triethylamine, 95 mL of tetrahydrofuran, and 60 g (281.6 mmol) of BOC anhydride was stirred at ambient temperature under $N_2$. Monitored by TLC (10% methanol in dichloromethane). After 15 minutes, solvent evaporated, dissolved in 100 mL dichloromethane, and washed with 2×50 mL $NH_4Cl$ (sat). Dried over $MgSO_4$, filtered, and evaporated. Purified on silica, eluting with dichloromethane to obtain 27.52 g of a clear beige oil.

To a solution of tert-butyl 2-hydroxyethyl(methyl)carbamate (24.52 g, 140 mmol) in 340 mL dichloromethane and 85 mL DMSO was added 39 mL (279.8 mmol) of triethylamine and the reaction mixture stirred at ambient temperature under $N_2$. To this was added 45 g (280 mmol) of pyridine sulfur trioxide, portionwise. Exotherm was observed and the solution became clear dark yellow. Cooled to 0° C. and stirred for 1 hour 20 minutes. Monitored by TLC (10% methanol in dichloromethane). Concentrated to a total volume of ~250 mL. Washed with 3×250 mL $H_2O$ then 250 mL NaCl (sat). Dried over $MgSO_4$, filtered, and solvent evaporated. Distilled at 75° C. (3 mm Hg) to provide 13.83 g of a clear liquid.

(4-(Methyl(2-(methylamino)ethyl)amino)phenyl)methyl-enediphosphonic acid

A deep yellow solution of diethyl 4-aminobenzylphosphonate 1 (20.0 g, 82.2 mmol) in 200 mL butyl formate was heated at reflux for 2 hours. Monitored by TLC (10% methanol/ethyl acetate). Solvent removed on a rotovap (40° C.) and further concentrated in vacuo to afford 22.3 g of 2 as a brown oil.

To a cooled (0° C.) flask containing 22.3 g (82.2 mmol) of 2, stirred under $N_2$, was added 100 mL (100 mmol) 1.0 M $BH_3$ in THF via cannula. Solution heated at reflux for 2 hours. Monitored by TLC (10% methanol/ethyl acetate). Cooled to 0° C. and quenched with 100 mL methanol. Solvent removed on a rotovap (40° C.). Acidified with 100 mL 1.0 N HCl, washed with 3×75 mL diethyl ether. Neutralized aqueous layer with $NaHCO_3$(sat) until pH=8. Extracted with 3×75 mL dichloromethane. Dried over $MgSO_4$, filtered, evaporated solvent, and further concentrated in vacuo to obtain 21.14 g of 3 as a clear yellow oil.

To a cooled (0° C.) solution of 3 (18.62 g, 72.3 mmol) in 150 mL dichloromethane, stirred under $N_2$, was added 20.1 mL (144.6 mmol) of trifluoroacetic anhydride, followed by 11.68 mL (144.6 mmol) of pyridine. Warmed to room temperature and stirred clear yellow solution under $N_2$ for 1 hour. Neutralized with 100 mL 10% $NaHCO_3$ solution. Washed organic layer with 50 mL NaCl (sat), 2×50 mL 10% $KHSO_4$ solution. Dried over $MgSO_4$, filtered, evaporated solvent, and further concentrated yellow oil in vacuo to obtain 25.5 g of 4 as a yellow oil.

To a cooled (−42° C.) solution of 4 (21.02 g, 59.5 mmol) in 50 mL dimethoxyethane, stirred under $N_2$, was added 100 mL (100 mmol) of 1.0 M LiHMDS in THF via cannula. Stirred at −42° C./$N_2$ for an additional 20 minutes then added, via syringe, 17.2 mL (110 mmol) of diethylchlorophosphate. Continued to stir dark red solution at −42° C./$N_2$ for 3 hours. Quenched with 75 mL 1.0N HCl. Warmed to room temperature, added 100 mL $H_2O$ (HPLC), washed aqueous layer with 2×125 mL ethyl acetate. Combined bright orange organic layer, dried over $MgSO_4$, filtered, and evaporated solvent. Crude material purified on silica in 0-10% methanol/ethyl acetate. Obtained 21.96 g of 5 as a light yellow solid: $^{31}P$ NMR (121 MHz, CDCl3) ☐ 18.2.

To a solution of 8.6 g (17.56 mmol) of 5 in 20 mL ethanol was added 24.27 g (176 mmol) of $K_2CO_3$. Stirred at room temperature/$N_2$ for 19 hours. Filtered, diluted with 75 mL $H_2O$(HPLC), and extracted with 2×75 mL dichloromethane. Dried over $MgSO_4$, filtered, evaporated solvent and further concentrated in vacuo to obtain 7.47 g of 6 as a yellow oil.

To a solution of 6 (4.6 g, 11.7 mmol) in 100 mL dichloromethane was added 8.03 g (17.5 mmol) BOC-aldehyde in 10 mL dichloromethane. Stirred at room temperature/$N_2$ for 1 hour. Added 5.19 g (23.4 mmol) of sodium acetoxyborohydride to the clear light yellow solution. Continued to stir cloudy yellow solution at room temperature/$N_2$ for 22 hours, monitored by HPLC. Diluted with 100 mL dichloromethane and washed with 3×50 mL $NaHCO_3$ (sat). Dried over $MgSO_4$, filtered, and evaporated solvent to obtain 12.3 g of a yellow liquid. Purified on silica in 0-10% methanol/dichloromethane to obtain 3.56 g of 7 as clear yellow oil: $^{31}P$ NMR (121 MHz, CDCl3) ☐ 19.8.

A solution of 7 (6.48 g, 11.8 mmol) in 45 mL 12 N hydrochloric acid was heated at reflux for 18 hours. Cooled to room temperature and concentrated under $N_2$. Precipitated solid with ethanol and evaporated excess solvent to obtain 8 as tan solid.

To a mixture of 8 (3.98 g, 12.4 mmol) in 30 mL DMSO was added 16.8 mL (68.0 mmol) of N,O-Bis(trimethylsilyl)acetamide. Exotherm was observed. Heated gently with heat gun until mixture was homogeneous. Added 2.5 mL (22.2 mmol) 3,5-lutidine and poured mixture into 400 mL methanol. Stirred vigorously over ice, filtered to obtain a solid. Washed with diethyl ether and dried in vacuo to obtain 3.55 g of 9 as an off-white solid: $^{31}$P NMR (121 MHz, D2O) ☐ 19.4.

Example 7

43-[(4-(Methyl(2-(methylamino)ethyl)amino)phenyl)methylenediphosphonic acid] rapamycin carbamate

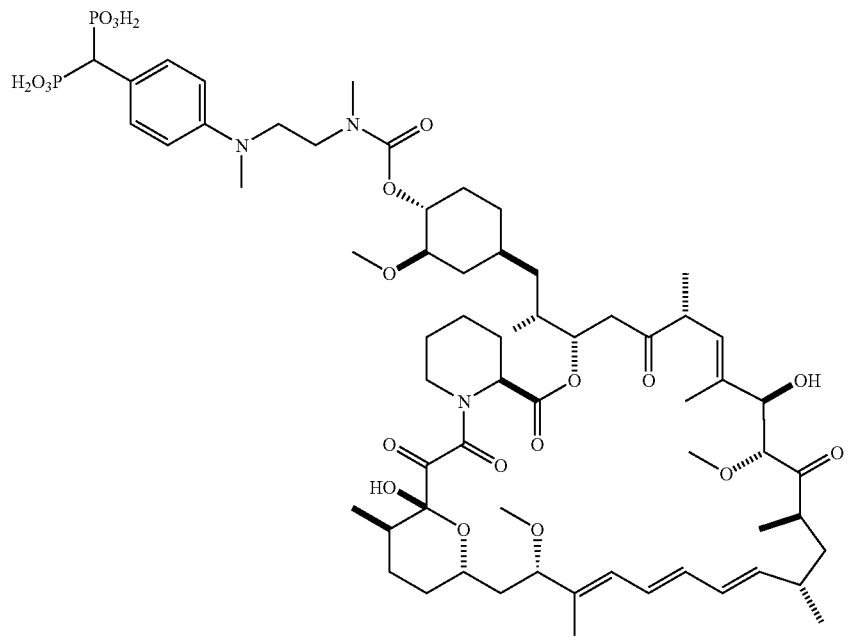

43-[(4-Nitrophenyl carbonate] rapamycin

To a cooled (0° C.) solution of rapamycin (20.0 g, 21.8 mmol) in 180 mL of dichloromethane, under an atmosphere of N$_2$, was added a solution of 4-nitrophenyl chloroformate (5.08 g, 25.2 mmol) in 30 mL DCM followed by neat 3,5-lutidine (2.91 g, 27.4 mmol), dropwise. The reaction solution was stirred at 0° C. for 30 min then transferred to a separatory funnel containing EtOAc (700 mL). The organic layer was washed successively with ice cold 1N HCl (2×150 mL; added small portions of brine to remove emulsions), saturated NaHCO$_3$ (2×150 mL), deionized H2O (1×100 mL), and brine (2×150 mL), then dried over MgSO$_4$ and concentrated. The crude product was purified by silica gel flash chromatography (eluted with 10-20% Acetonitrile/DCM) to provide 17.9 g of a pale yellow solid: 1078 m/z (M-H).

The title compound may be synthesized as follows: A mixture of (4-(methyl(2-(methylamino)ethyl)amino)phenyl)methylenediphosphonic acid (4.5 mmol) and N,O-bis(trimethylsilyl)acetamide (BSA; 3.05 g, 15.0 mmol) in 10 mL of DMSO is heated periodically with a heat gun until all solids dissolved. Stirring at ambient temperature is continued for 1 h, upon which a solution of 43-[(4-nitrophenyl carbonate] rapamycin (3.2 g, 3.0 mmol) in 5 mL DMSO is added followed immediately by neat 3,5-lutidine (0.48 g, 4.5 mmol). The resulting reaction solution is stirred at ambient temperature until reaction is complete by HPLC. The reaction solution is diluted with acetonitrile (90 mL) then transferred to a 2-L Erlenmeyer flask. Vigorous stirring is begun and 0.1M HCl is added slowly to the solution till pH of this solution reaches ~3. Stirring is continued for 15 minutes after which 100 mM phosphate buffer (90 mL; pH 6.8) is added to quench further reactivity. The solution is treated with Amberchrom resin (60 mL slurry; pre-washed with water and acetone) and stirred under a steady stream of N$_2$ to remove organic volatiles and the aqueous solvent is removed via suction filtration. The resin bed is washed with water to remove inorganic salts. The vacuum is then maintained so that the maximum amount of water can be removed from the resin bed. The resin is then washed with diethyl ether to remove remaining starting material. The crude product is eluted with acetone. The eluate is concentrated in vacuo and the residue purified by prep HPLC to give a white solid: $^{31}$P NMR (121 MHz, Acetonitrile-D3/D2O) ☐ 22.2; 1277 m/z (M-H).

Example 8

Scheme for (Hydroxy(4-(methyl(2-(methylamino)ethyl)amino)phenyl)phosphoryl)methylphosphonic acid

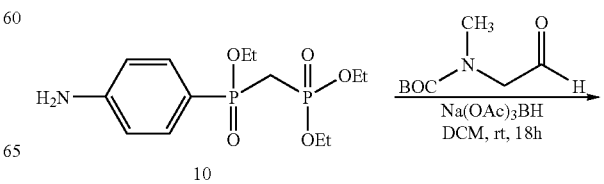

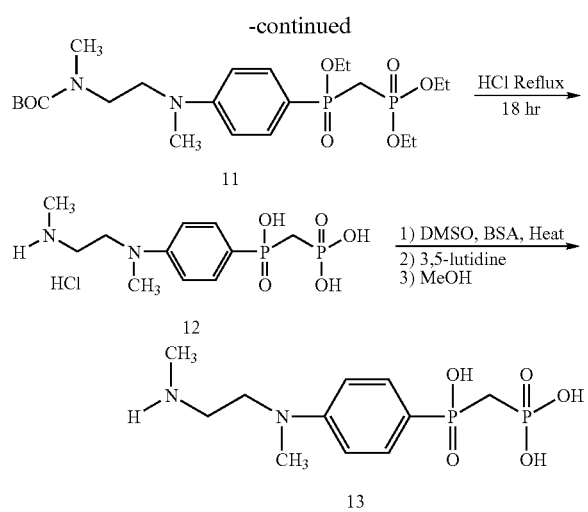

(Hydroxy(4-(methyl(2-(methylamino)ethyl)amino)
phenyl)phosphoryl)methylphosphonic acid

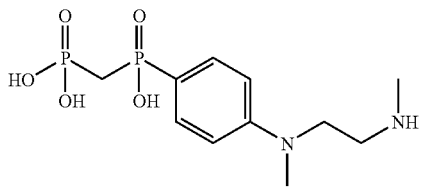

(Hydroxy(4-(methyl(2-(methylamino)ethyl)amino)
phenyl)phosphoryl)methylphosphonic acid To a solution of 10 [[(4-aminophenyl-ethoxyphosphinyl]
methyl]-phosphonic acid diethyl ester (CAS#: 344585-22-4) (3.66 g, 10.5 mmol) in 25 mL dichloromethane was added 3.64 g (21.0 mmol) BOC aldehyde. To the clear yellow solution was then added 5.33 g (24.0 mmol) sodium triacetoxyborohydride. Cloudy white solution stirred for 18 hours at room temperature, under $N_2$. Monitored by HPLC and TLC (10% methanol/ethyl acetate). Diluted in 50 mL dichloromethane, washed with 3×50 mL $NaHCO_3$ (sat). Dried organic layer over $MgSO_4$, filtered, and evaporated solvent. Purified on silica in 5% methanol/dichloromethane to obtain 5.47 g of 11 as a yellow oil: $^{31}$P NMR (121 MHz, DMSO-d6) □ 34.9, 20.4.

A solution of 11 (5.47 g, 6.47 mmol) in 150 mL 12.0 N hydrochloric acid was heated at reflux for 2 hours. Cooled to room temperature and concentrated under $N_2$. Precipitated solid with ethanol and evaporated solvent to obtain a tan solid. Added 50 mL $H_2O$(HPLC) and heated at reflux for 40 minutes. Concentrated under $N_2$ at 60° C. to obtain a clear glassy solid. Added 50 mL toluene and evaporated, repeated until beige solid was obtained. Filtered and washed with diethyl ether to obtain 12 as a beige solid.

To a mixture of 12 (1.07 g, 3.32 mmol) in 11 mL DMSO was added 4.5 mL (18.3 mmol) N,O-Bis(trimethylsilyl)acetamide. Heated gently with heat gun until mixture was homogeneous. Added 0.7 mL (6.23 mmol) 3,5-lutidine. Poured mixture in 200 mL methanol. Stirred vigorously over ice and filtered to obtain white solid. Washed with diethyl ether and concentrated in vacuo to obtain 13 as an off-white solid: $^{31}$P NMR (121 MHz, DMSO-d6) □ 37.4, 20.1.

Example 9

43-[(Hydroxy(4-(methyl(2-(methylamino)ethyl)
amino)phenyl)phosphoryl) methylphosphonic acid]
rapamycin carbamate

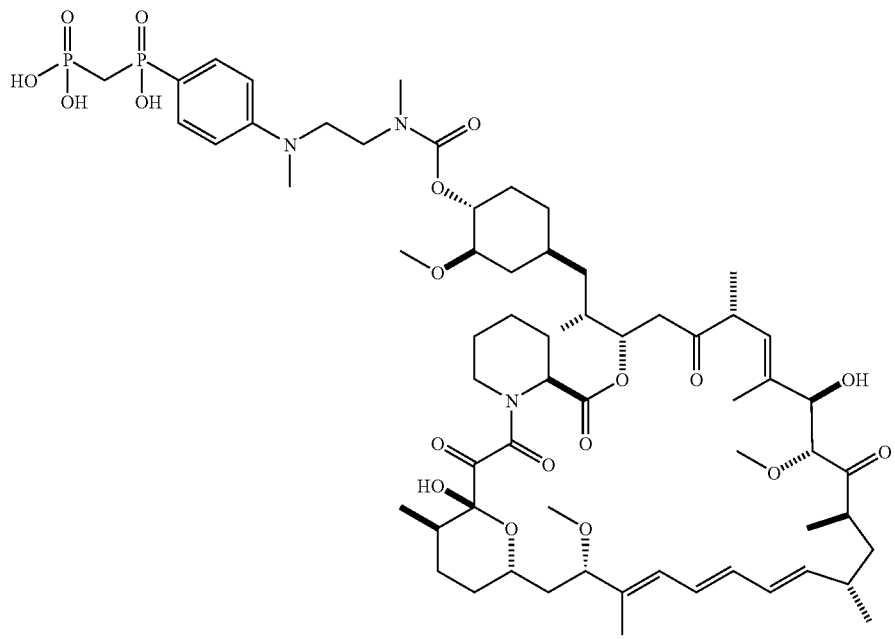

The title compound was synthesized in a manner similar to that described for Example 3, using (hydroxy(4-(methyl(2-(methylamino)ethyl)amino)phenyl)phosphoryl)methylphosphonic acid. The product was obtained as a white solid: $^{31}$P NMR (121 MHz, Acetonitrile-D3/D2O☐ 31.4, 21.5; 1261 m/z (M-H).

General Description of Prep HPLC Method

A filtered (NALGENE® PTFE non-sterile filter, 25 mm, 0.45 µm) solution of crude product in acetone/phosphate buffer was injected onto a preparative HPLC column (PLRP-S) and eluted with Acetonitrile/phosphate buffer (with EDTA). The final product was then isolated via resin capture (using Amberchrom® resin) in a similar manner as described in Example 3.

Example 10

Hydroxyapatite Assay

Hydroxyapatite is the principal mineral component of bone. Hydroxyapatite adsorption chromatography is used as an assay to evaluate the bone-targeting potential of a compound.

Method: The rentention time of a test compound is measured using a linear gradient from 10 mM sodium phosphate, 0.15 N NaCl, pH=6.8 to 500 mM sodium phosphate, 0.15 N NaCl, pH=-6.8 on a TSK-Gel HA 1000 high pressure liquid chromatography column (7.5 mm×75 mm). The rentention time of the compound is expressed in terms of K=(retention time–void time)/void. This K value is corrected using two reference compounds to correct from inter-column and inter-system variation to obtain a K' value.

Reference Compounds: K' values were determined for known bone targeted compounds, the bisphosphonate, alendronate and tetracycline. Alendronate gave a K' value of 3.7 and tetracycline gave a K' value of 2.0.

Example 11

In Vivo Anti-Resorptive Testing in Hypercalcemic Mouse

A mouse hypercalcemia model for determining the efficacy of inhibitors of bone resorption may be used to compare compounds of this invention. This model exploits the intrinsic effects of PTH (1-34) to stimulate the resorptive activity of osteoclasts in vivo. In one version of the assay, compounds are injected into mice subcutaneously, once or twice per day for five consecutive days. On the third day of compound treatments, PTH administration begins. PTH (20 µg/kg) is given four times per day, subcutaneously, until the end of the study. Control animals receive PTH but do not receive test compounds. Blood samples are collected from the animals to obtain baseline (pre-PTH treatment), 48 hour and 72 hour (after initiation of PTH treatment) serum samples. The serum samples are analyzed for calcium concentration using the quantitative calorimetric assay reagent Arsenazo III (Sigma). Calcium serum levels for treated groups are compared to calcium serum levels of control groups and a percentage of inhibition of hypercalcemia is calculated for each time point. When a compound is effective in inhibiting the activity of osteoclasts, observed serum calcium concentrations are lower than in animals that receive only PTH in the absence of test compound.

Example 12

Cytoxicity and Inhibition of Tumor Growth

Compounds may be assayed for anti-tumor activity using in vivo and in vitro assays which are well known to those skilled in the art. Generally, initial screens of compounds to identify candidates for anti-cancer drugs are performed in cellular in vitro assays. Compounds identified as having anti-cell proliferative activity can then be subsequently assayed in whole organisms for anti-tumor activity and toxicity. The initial screens are preferably cellular assays which can be performed rapidly and cost-effectively relative to assays that use whole organisms. For purposes of the present invention, the term "anti-proliferative compound" is used to mean compounds having the ability to impede or stop cells from progressing through the cell cycle and dividing. For purposes of the present invention, the terms "anti-tumor" and "anti-cancer" activity are used interchangeably.

Methods for determining cell proliferation are well known and can be used to identify compounds with anti-proliferative activity. In general, cell proliferation and cell viability assays are designed to provide a detectable signal when cells are metabolically active. Compounds are tested for anti-cell proliferation activity by assaying for a decrease in metabolic activity. Commonly used methods for determining cell viability depend upon, for example, membrane integrity (e.g. trypan blue exclusion) or incorporation of nucleotides during cell proliferation (e.g. BrdU or 3H-thymidine).

Preferred methods of assaying cell proliferation utilize compounds that are converted into a detectable compound during cell proliferation. Particularly preferred compounds are tetrazolium salts and include without limitation MTT (3-(4,5-dimethylthiazol-2-yl)-2,5-diphenyltetrazolium bromide; Sigma-Aldrich, St. Louis, Mo.), MTS (3-(4,5-dimethylthiazol-2-yl)-5-(3-carboxymethoxyphenyl)-2-(4-sulfophenyl)-2H-tetrazolium), XTT (2,3-bis(2-Methoxy-4-nitro-5-sulfophenyl)-2H-tetrazolium-5-carboxanilide), INT, NBT, and NTV (Bernas et al. Biochim Biophys Acta 1451(1):73-81, 1999). Preferred assays utilizing tetrazolium salts detect cell proliferation by detecting the product of the enzymatic conversion of the tetrazolium salts into blue formazan derivatives, which are readily detected by spectroscopic methods (Mosman. J. Immunol. Methods. 65:55-63, 1983).

Generally, preferred methods for assaying cell proliferation involve incubating cells in a desired growth medium with and without the compounds to be tested. Growth conditions for various prokaryotic and eukaryotic cells are well-known to those of ordinary skill in the art (Ausubel et al. Current Protocols in Molecular Biology. Wiley and Sons. 1999; Bonifacino et al. Current Protocols in Cell Biology. Wiley and Sons. 1999 both incorporated herein by reference). To detect cell proliferation, the tetrazolium salts are added to the incubated cultured cells to allow enzymatic conversion to the detectable product by active cells. Cells are processed, and the optical density of the cells is determined to measure the amount of formazan derivatives. Furthermore, commercially available kits, including reagents and protocols, are availabe for examples, from Promega Corporation (Madison, Wis.), Sigma-Aldrich (St. Louis, Mo.), and Trevigen (Gaithersburg, Md.).

Any cultured cell line may be used to screen compounds for antiproliferative activity. In certain embodiments of the invention cell lines utilized include, but are not limited to, Exemplary cell lines utilized for the determination of the ability of inventive compounds to inhibit cellular proliferation include, but are not limited to COLO 205 (colon cancer), DLD-1 (colon cancer), HCT-15 (colon cancer), HT29 (colon cancer), HEP G2 (Hepatoma), K-562 (Leukemia), A549 (Lung), NCI-H249 (Lung), MCF7 (Mammary), MDA-MB-231 (Mammary), SAOS-2 (Osteosarcoma), OVCAR-3 (Ovarian), PANC-1 (Pancreas), DU-145 (Prostate), PC-3 (Prostate), ACHN (Renal), CAKI-1 (Renal), MG-63 (Sarcoma).

Preferably, the cell line is a mammalian, but is not limited to mammalian cells since lower order eukaryotic cells such as yeast may also be used to screen compounds. Preferred mammalian cell lines are derived from humans, rats, mice, rabbits, monkeys, hamsters, and guinea pigs since cells lines from these organisms are well-studied and characterized. However, the present invention does not limit the use of mammalians cells lines to only the ones listed.

Suitable mammalian cell lines are often derived from tumors. For example, the following tumor cell-types may be sources of cells for culturing cells: melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Non-limiting examples of mammalian cells lines that have been widely used by researchers include HeLa, NIH/3T3, HT1080, CHO, COS-1, 293T, WI-38 and CV1/EBNA-1.

Other in vitro cellular assays may be used which rely upon a reporter gene to detect metabolically active cells. Non-limiting examples of reporter gene expression systems include green fluorescent protein (GFP), and luciferase. As an example of the use of GFP to screen for potential antitumor drugs, Sandman et al. (Chem Biol. 6:541-51; incorporated herein by reference) used HeLa cells containing an inducible variant of GFP to detect compounds that inhibited expression of the GFP, and thus inhibited cell proliferation.

Compounds identified by in vitro cellular assays as having anti-cell proliferation activity are then tested for anti-tumor activity in whole organisms. Preferably, the organisms are mammalian. Well-characterized mammalians systems for studying cancer include rodents such as rats and mice. Typically, a tumor of interest is transplanted into a mouse having a reduced ability to mount an immune response to the tumor to reduce the likelihood of rejection. Such mice include for example, nude mice (athymic) and SCID (severe combined immunodeficiency) mice. Other transgenic mice such as oncogene containing mice may be used in the present assays (see for example U.S. Pat. No. 4,736,866 and U.S. Pat. No. 5,175,383). For a review and discussion on the use of rodent models for antitumor drug testing see Kerbel (Cancer Metastasis Rev. 17:301-304, 1998-99).

In general, the tumors of interest are implanted in a test organism preferably subcutaneously. The organism containing the tumor is treated with doses of candidate anti-tumor compounds. The size of the tumor is periodically measured to determine the effects of the test compound on the tumor. Some tumor types are implanted at sites other than subcutaneous sites (e.g. intraperitoneal sites) and survival is measured as the endpoint. Parameters to be assayed with routine screening include different tumor models, various tumor and drug routes, and dose amounts and schedule. For a review of the use of mice in detecting antitumor compounds see Corbett et al. (Invest New Drugs. 15:207-218, 1997; incorporated herein by reference)

Example 13

Biological Activity

A. Inhibition of Proliferation of HT1080 Human Fibrosarcoma Cells; FKBP-Binding

Compounds of this invention which were tested for inhibitory activity on the proliferation of HT1080 cells yielded IC25 values of 20 nM, retaining still significant activity of the parent molecule, rapamycin (IC25=0.1 nM), and exhibiting far greater potency than that seen with the bisphosphonates Zolendronate and Alendronate on osteosarcoma cells (IC50 values of 7-75 $\mu$M). One of the compounds was tested for FKBP-binding and was found to have an IC50 of 5 nM in a conventional FKBP-binding assay, only slightly off rapamycin's 1 nM IC50.

B. Inhibition of Osteoclasts Formation (Non-Bone)

Compounds of this invention which were tested for inhibitory activity on the formation of osteoclasts provided IC50 values of 10-100 nM, retaining significant activity of the parent molecule, rapamycin (IC50=1-10 nM), and exhibiting far greater potency than that seen with Zolendronate and Alendronate (IC50=1-10 $\mu$M).

C. Demonstration of Antiresorptive Activity in Hypercalcemic Mice

Compounds of this invention which were tested for inhibition of PTH-induced hypercalcemia in a 5-day mouse study demonstrated activity as good as or better than rapamycin in initial studies. One of the compounds demonstrated significant and sustained reduction (~70%) of serum calcium levels when dosed at 10 mg/kg (bid, IP). It also demonstrated similar inhibition with a single oral dose of 50 mg/kg (IP).

In a separate experiment in PTH-induced hypercalcemic mice, the compound demonstrated superior reduction (83%, Day 5) of serum calcium levels when dosed at 10 mg/kg (bid, IP) compared to rapamycin dosed similarly (38% inhibition, Day 5).

In that study, mice were administered test compounds or vehicle twice daily by the intraperitoneal route of administration for five consecutive days. Baseline serum calcium was measured on Day 2. Parathyroid hormone was administered subcutaneously at a dose of 20 $\mu$g/kg, four times a day, on Days 3, 4, and 5 to drug treatment and vehicle control groups. Serum calcium levels were measured on Days 4 and 5.

A second compound of this series, also produced per the foregoing examples, was found to have very favorable FKBP-binding activity (IC50=3 nM) and demonstrated extremely potent activity in our mouse hypercalcimia assay, with inhibition equal to or greater than equivalent (molar) doses of rapamycin (as low as 0.3 mg/kg, daily IP).

These results demonstrate the achievement of dual in vitro antiproliferative and antiresorptive effects with compounds of this invention containing aliphatic and aromatic groups Q. Both types of compounds demonstrated potent and sustained inhibition of PTH-induced hypercalcemia in mice.

The invention claimed is:

1. A compound of the Formula I:

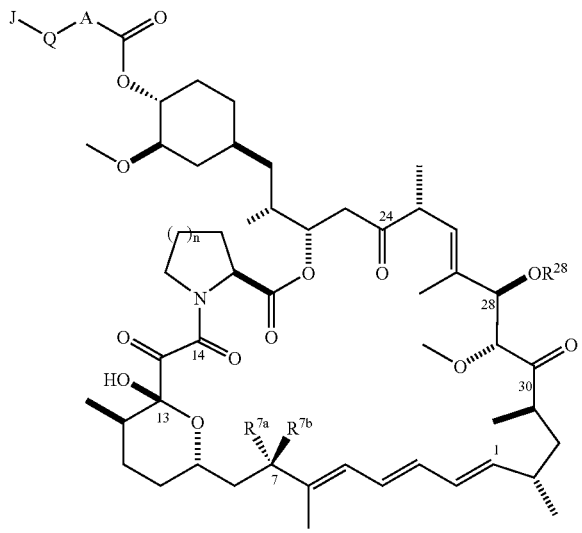

wherein:
A is independently —O—, —S— or —NR$^2$—;
Q is V or VN(R)V; wherein V is independently an aliphatic, a heteroaliphatic, an aryl or a 5-14 membered heteroaryl moiety, having 1-4 heteroatoms selected from nitrogen, oxygen and sulfur;
J is:

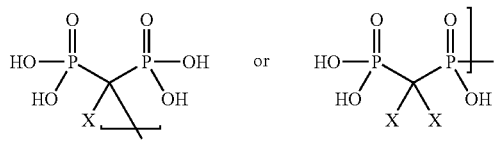

each occurrence of X is independently H, —NR$^2$R$^5$, —OR$^2$ or halo;
one of R$^{7a}$ and R$^{7b}$ is H and the other is H, halo, —R$^A$, —OR$^A$, —SR$^A$, —OC(O)R$^A$, —OC(O)NR$^A$R$^B$, —NR$^A$R$^B$, —NR$^B$C(O)R$^A$, —NR$^B$C(O)OR$^A$, —NR$^B$SO$_2$R$^A$, —OC(O)OR$^A$, —NR$^B$C(O)NR$^A$R$^B$ or —NR$^B$SO$_2$NR$^A$R$^{Bt}$; or R$^{7a}$ and R$^{7b}$, taken together, are H in the tetraene moiety:

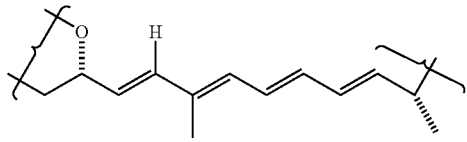

R$^A$ is R$^2$, R$^B$ is OH or R$^2$;
R, R$^2$ and R$^5$ are independently selected from H, an aliphatic, a heteroaliphatic, an aryl and a 5-14 membered heteroaryl moiety having 1-4 heteroatoms selected from nitrogen, oxygen and sulfur;
R$^{28}$ is hydrogen, —COVH or COAQJ;
and n is 1 or 2;
wherein each aliphatic moiety contains 1-8 contiguous aliphatic carbon atoms, each heteroaliphatic moiety is an aliphatic moiety which contains an O, S, N, P or Si atom in place of one or more carbon atoms; and each of the foregoing aliphatic and heteroaliphatic moieties is independently branched or unbranched, or cyclic or acyclic, and unsubstituted or substituted with one or more groups selected from halogen, —YR$^2$, —Y—C(=O)R$^2$, —NR$^2$C(=O)R$^5$, —NR$^2$C(=O)NR$^5$, —NR$^2$C(=O)OR$^5$, —NR$^2$C(=NH)NR$^5$, —Y—C(=O)OR$^2$, —Y—C(=O)NR$^2$R$^5$, —Y—C(=NR$^2$)NR$^2$R$^5$, —CO-COR$^2$, —C(=O)(CH$_2$)$_r$C(=O)R$^2$, J, —CN, —S(=O)R$^2$, —SO$_2$R$^2$, —SO$_2$NR$^2$R$^5$, —NO$_2$, —NR$^5$SO$_2$R$^2$, —OSO$_2$R$^2$, —NR$^5$SO$_2$NR$^2$R$^5$, =O, =S, =NR$^2$, =NNR$^2$R$^5$, =NNHC(O)R$^2$, =NNHCO$_2$R$^2$, and =NNHSO$_2$R$^2$, wherein Y is selected from a bond, —O—, NR$^5$, and —S—, r is an integer of 1 to 4;

and each aryl or heteroaryl moiety is independently unsubstituted or substituted with one or more groups selected from halogen, —YR$^2$, —Y—C(=O)R$^2$, —NR$^2$C(=O)R$^5$, —NR$^2$C(=O)NR$^5$, —NR$^2$C(=O)OR$^5$, and —NR$^2$C(=NR$^2$)NR$^5$, —Y—C(=O)OR$^2$, —Y—C(=O)NR$^2$R$^5$, —Y—C(=NR$^2$)NR$^2$R$^5$, —COCOR$^2$, —C(=O)(CH$_2$)$_r$C(=O)R$^2$, J, —CN, —S(=O)R$^2$, —SO$_2$R$^2$, —SO$_2$NR$^2$R$^5$, —OSO$_2$R$^2$, —NO$_2$, —NR$^5$SO$_2$R$^2$ and —NR$^5$SO$_2$NR$^2$R; wherein Y is selected from a bond, —O—, NR$^5$ and —S—, r is an integer of 1 to 4.

2. A compound of the Formula II:

Formula II

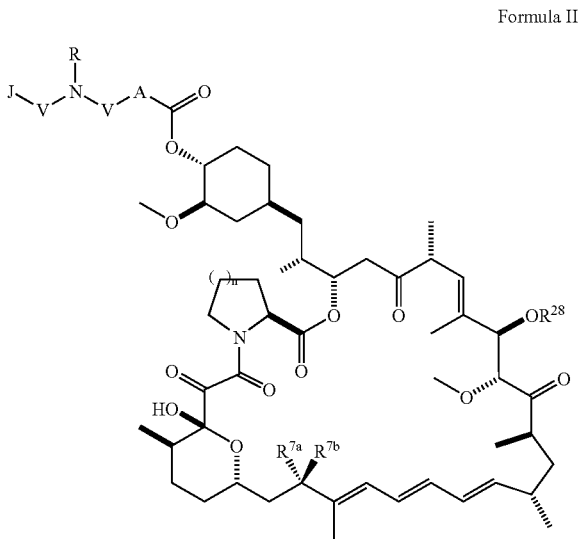

wherein:
A is independently —O—, —S— or —NR$^2$—;
V is selected from the groups consisting of an aliphatic, a heteroaliphatic, an aryl and a 5-14 membered heteroaryl moiety, having 1-4 heteroatoms selected from nitrogen, oxygen and sulfur;
J is:

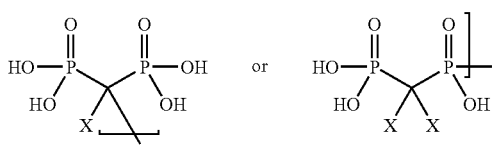

each occurrence of X is independently H, —NR$^2$R$^5$, —OR$^2$ or halo;
one of R$^{7a}$ and R$^{7b}$ is H and the other is H, halo, —R$^A$, —OR$^A$, —SR$^A$, —OC(O)R$^A$, —OC(O)NR$^A$R$^B$, —NR$^A$R$^B$, —NR$^B$C(O)R$^A$, —NR$^B$C(O)OR$^A$, —NR$^B$SO$_2$R$^A$, —OC(O)OR$^A$, —NR$^B$C(O)NR$^A$R$^B$, or —NR$^B$SO$_2$NR$^A$R$^{Bt}$; or R$^{7a}$ and R$^{7b}$, taken together, are H in the tetraene moiety:

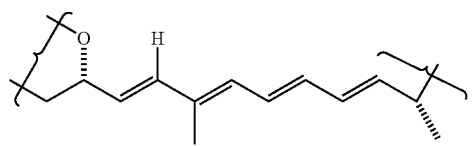

- $R^A$ is $R^2$, $R^B$ is OH or $R^2$, (in some cases one or both of $R^A$ and $R^B$ is H);
- R, $R^2$ and $R^5$ are independently selected from H, an aliphatic, a heteroaliphatic moiety, an aryl and a 5-14 membered heteroaryl moiety having 1-4 heteroatoms selected from nitrogen, oxygen and sulfur;
- $R^{28}$ is hydrogen, —COVH or COAQJ;
- and n is 1 or 2;
- wherein each aliphatic moiety contains 1-8 contiguous aliphatic carbon atoms, each heteroaliphatic moiety is an aliphatic moiety which contains an O, S, N, P or Si atom in place of one or more carbon atoms; and each of the foregoing aliphatic and heteroaliphatic moieties is independently branched or unbranched, or cyclic or acyclic, and unsubstituted or substituted with one or more groups selected from halogen, —$YR^2$, —Y—C(=O)$R^2$, —$NR^2$C(=O)$R^5$, —$NR^2$C(=O)$NR^5$, —$NR^2$C(=O)$OR^5$, —$NR^2$C(=NH)$NR^5$, —Y—C(=O)$OR^2$, —Y—C(=O)$NR^2R^5$, —Y—C(=$NR^2$)$NR^2R^5$, —CO-$COR^2$, —C(=O)$(CH_2)_rC$(=O)$R^2$, J, —CN, —S(=O)$R^2$, —$SO_2R^2$, —$SO_2NR^2R^5$, —$NO_2$, —$NR^5SO_2R^5$, —$OSO_2R^2$, —$NR^5SO_2NR^2R^5$, =S, =$NR^2$, =$NNR^2R^5$, =NNHC(O)$R^2$, =$NNHCO_2R^2$, and =$NNHSO_2R^2$, wherein Y is selected from a bond, —O—, $NR^5$ and —S—, r is an integer of 1 to 4;
- and each aryl or heteroaryl moiety is independently unsubstituted or substituted with one or more groups selected from halogen, —$YR^2$, —Y—C(=O)$R^2$, —$NR^2$C(=O)$R^5$, —$NR^2$C(=O)$NR^5$, —$NR^2$C(=O)$OR^5$, and —$NR^2$C(=$NR^2$)$NR^5$, —Y—C(=O)$OR^2$, —Y—C(=O)$NR^2R^5$, —Y—C(=$NR^2$)$NR^2R^5$, —$COCOR^2$, —C(=O)$(CH_2)_rC$(=O)$R^2$, J, —CN, —S(=O)$R^2$, —$SO_2R^2$, —$SO_2NR^2R^5$, —$NO_2$, —$NR^5SO_2R^2$ and —$NR^5SO_2NR^2R$; wherein Y is selected from a bond, —O—, $NR^5$ and —S—, r is an integer of 1 to 4.

3. The compound of claim 2 having the formula II(a):

Formula II(a)

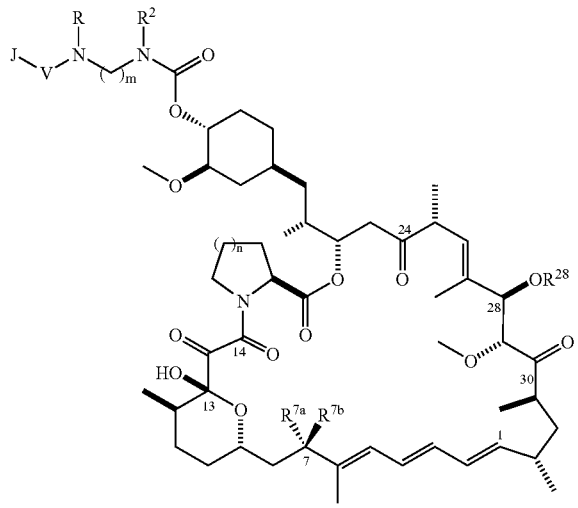

in which m is an integer from 2 through 8.

4. The compound of claim 3 having the formula II(b):

Formula II(b)

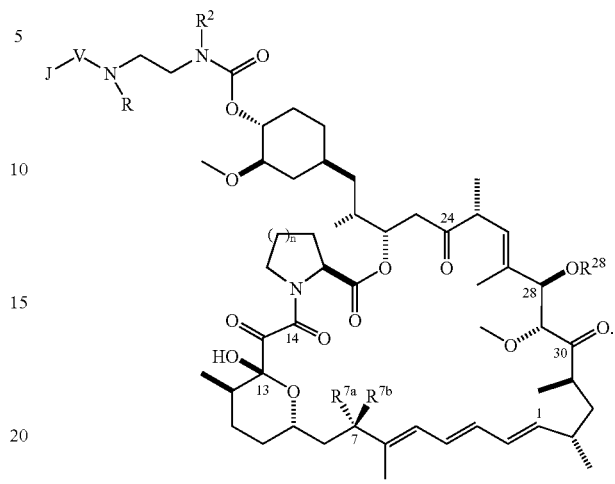

5. The compound of claim 3 having the formula II(d):

Formula II(d)

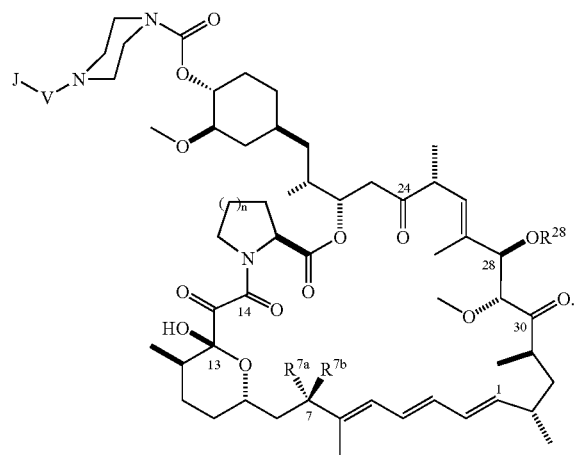

6. The compound of claim 2 having the formula II(e):

Formula II(e)

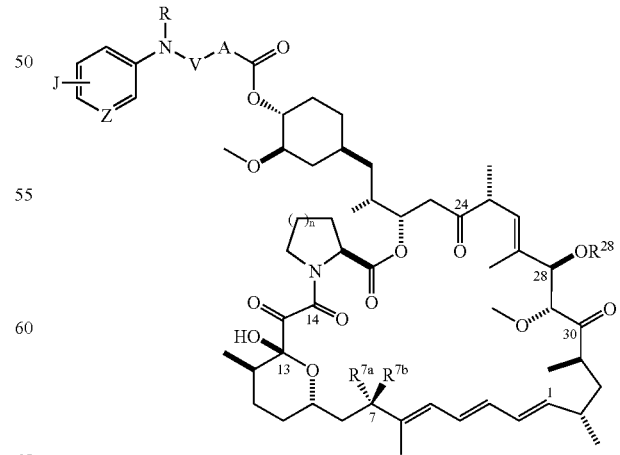

wherein Z is CH or N.

7. The compound of any of claims 3, 4 and 6 wherein one or both of R and $R^2$ groups are H.

8. The compound of any of claims 3, 4 and 6 wherein one or both R and $R^2$ groups are C1-C8 alkyl groups.

9. The compound of any of claims 3, 4 and 6 wherein one or both R and $R^2$ groups are $CH_3$.

10. The compound of any of claims 1-6 wherein n is 2; $R^{28}$ is H; $R^{7a}$ is OMe and $R^{7b}$ is H.

11. The compound of claim 4 having the formula II(f):

and wherein p is 0, 1, 2, 3, 4 or 5 and Z is N or CH.

12. The compound of claim 1 of the formula III(a):

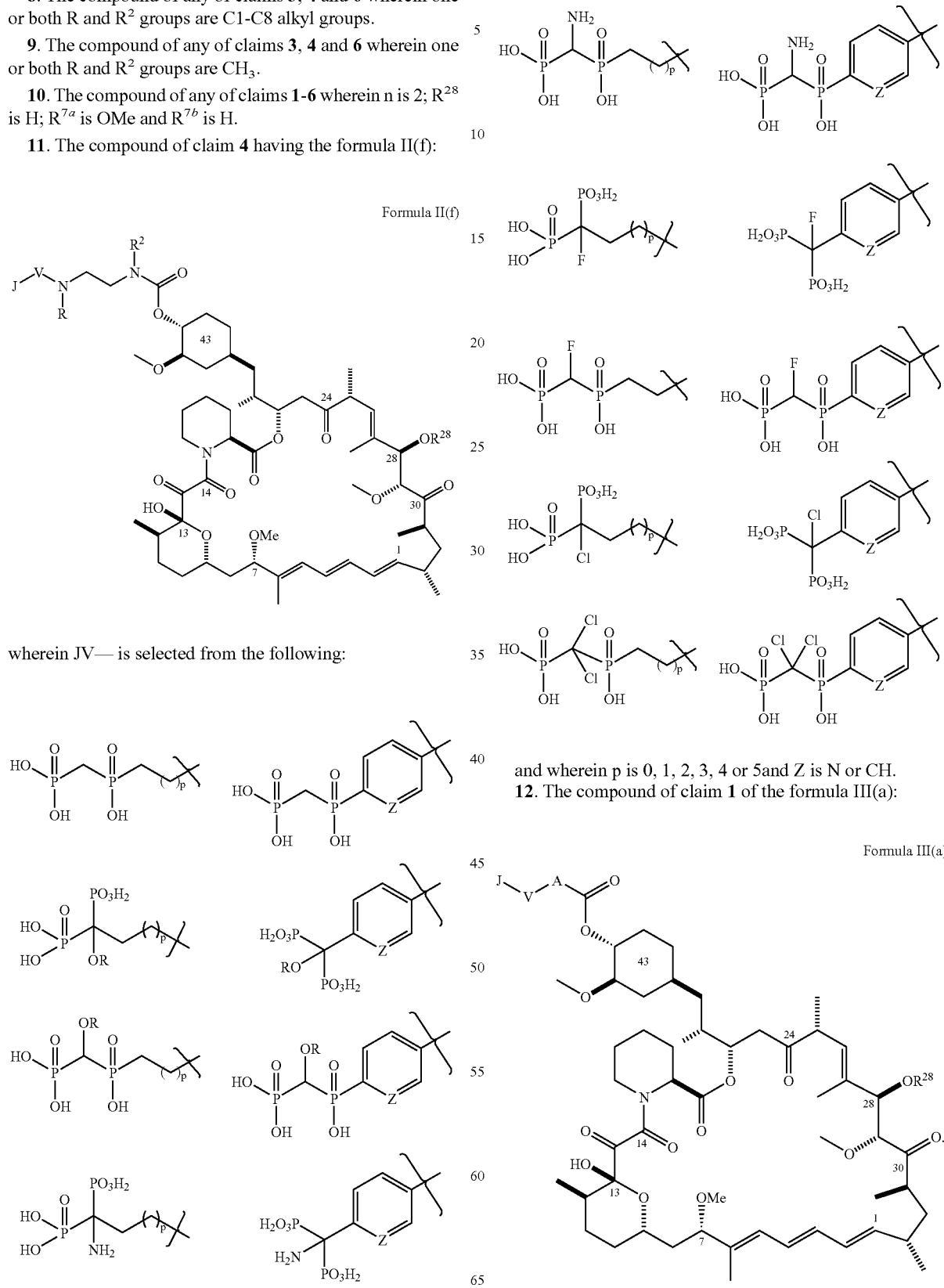

13. The compound of claim 12 wherein A is O or $NR^2$.
14. The compound of claim 12 wherein V is a 1-8-carbon alkyl moiety.
15. The compound of claim 12 wherein V is an aryl or a 5-14 membered heteroaryl moiety having 1-4 heteroatoms selected from nitrogen, oxygen, or sulfur.
16. The compound of claim 12 of the formula III(b):
Formula III(b)
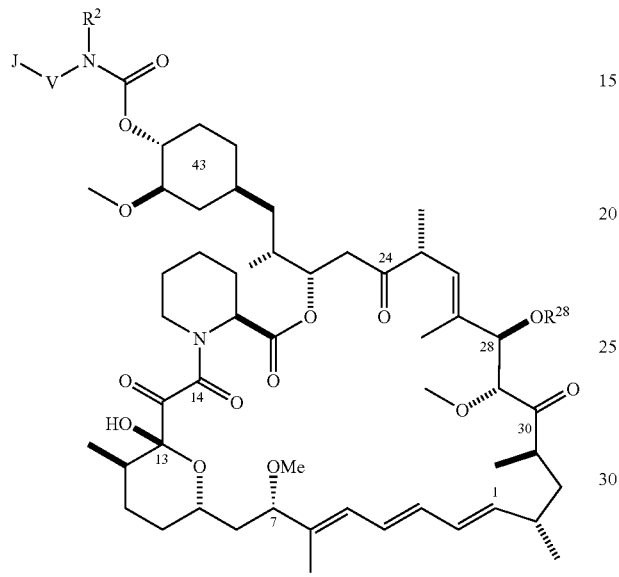
wherein $JVNR^2$—C(O)— is selected from the following:
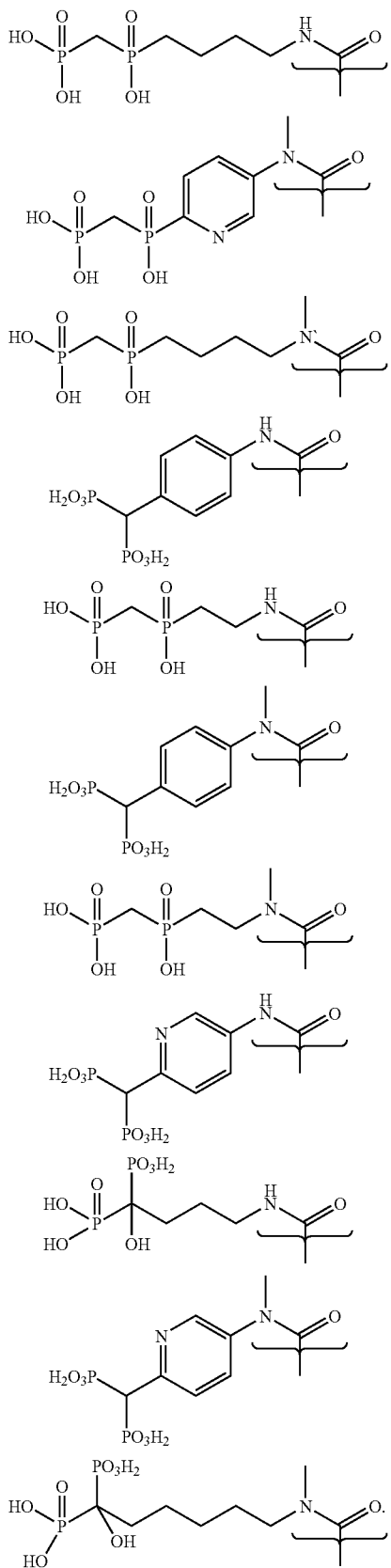

17. The compound of claim 12 of the formula III(c):

*Formula III(c)* wherein JVOC(O)— is selected from:

18. A composition comprising a compound of claim 1, together with a pharmaceutically acceptable vehicle and optionally containing one or more pharmaceutically acceptable excipients.

* * * * *